US 6,728,567 B2

(12) United States Patent
Rather et al.

(10) Patent No.: US 6,728,567 B2
(45) Date of Patent: Apr. 27, 2004

(54) METHOD AND APPARATUS FOR HIGH-RESOLUTION DETECTION AND CHARACTERIZATION OF MEDICAL PATHOLOGIES

(75) Inventors: John D. G. Rather, Grosse Pointe, MI (US); H. John Caulfield, Cornersville, TN (US); Richard D. Doolittle, Bethesda, MD (US); Peter J. Littrup, Bloomfield Hills, MI (US); Glenn W. Zeiders, Huntsville, AL (US)

(73) Assignee: Barbara Ann Karmanos Cancer Institute, Detroit, MI (US)

( * ) Notice: Subject to any disclaimer, the term of this patent is extended or adjusted under 35 U.S.C. 154(b) by 312 days.

(21) Appl. No.: 09/994,025

(22) Filed: Nov. 27, 2001

(65) Prior Publication Data

US 2002/0065466 A1 May 30, 2002

Related U.S. Application Data

(63) Continuation of application No. 09/272,452, filed on Mar. 19, 1999, now Pat. No. 6,385,474.
(60) Provisional application No. 60/078,788, filed on Mar. 20, 1998.

(51) Int. Cl.$^7$ .............................. A61N 7/02; A61B 5/00
(52) U.S. Cl. ....................... 600/407; 600/408; 600/439; 601/3
(58) Field of Search ................................. 600/407, 408, 600/437–439; 128/920, 922–925; 601/2, 3; 382/128; 706/20, 924

(56) References Cited

U.S. PATENT DOCUMENTS

| 3,154,067 | A | 10/1964 | Stenstrom et al. |
| 3,881,466 | A | 5/1975 | Wilcox |
| 3,886,489 | A | 5/1975 | Jones |
| 4,028,934 | A | 6/1977 | Sollish |
| 4,059,010 | A | 11/1977 | Sachs |
| 4,075,883 | A | 2/1978 | Glover |
| 4,222,274 | A | 9/1980 | Johnson |
| 4,317,369 | A | 3/1982 | Johnson |
| 4,363,326 | A | 12/1982 | Kopel |
| 4,412,288 | A | 10/1983 | Herman |
| 4,481,948 | A | 11/1984 | Sole |
| 4,515,165 | A | 5/1985 | Carroll |
| 4,542,744 | A | 9/1985 | Barnes et al. |
| 4,564,019 | A | 1/1986 | Miwa |
| 4,606,342 | A | 8/1986 | Zamba et al. |
| 4,662,222 | A | 5/1987 | Johnson |
| 4,671,256 | A | 6/1987 | Lemelson |
| 4,855,911 | A | 8/1989 | Lele et al. |
| 4,858,124 | A | 8/1989 | Lizzi et al. |

(List continued on next page.)

FOREIGN PATENT DOCUMENTS

| AU | 34432/95 | 5/1996 |
| EP | 284055 | 9/1988 |
| EP | 317049 | 5/1989 |

(List continued on next page.)

*Primary Examiner*—Shawna J Shaw
(74) *Attorney, Agent, or Firm*—Townsend and Townsend and Crew LLP

(57) ABSTRACT

The present invention relates to a method and apparatus for the construction and/or use of multidimensional fields that can be used for high-resolution detection and characterization of features within objects. The multidimensional field is constructed from data that is collected by an array of radiation detectors that substantially surround the object under study. The detected radiation is produced by an array of radiation sources and is subsequently scattered, reflected, transmitted, or diffracted by the object under study and any features within the object under study. In particular embodiments of the invention, the radiation that is used is ultrasonic radiation and the object under study is human or animal tissue or an organ. In this case, the invention permits the detection and identification of cancer by an intelligently trained evaluation system.

19 Claims, 9 Drawing Sheets

U.S. PATENT DOCUMENTS

| | | |
|---|---|---|
| 4,917,096 A | 4/1990 | Englehart et al. |
| 4,941,474 A | 7/1990 | Pratt, Jr. |
| 5,003,979 A | 4/1991 | Merickel et al. |
| 5,025,792 A | 6/1991 | Hon et al. |
| 5,029,476 A | 7/1991 | Metala et al. |
| RE33,672 E | 8/1991 | Miwa |
| 5,143,069 A | 9/1992 | Kwon et al. |
| 5,158,071 A * | 10/1992 | Umemura et al. ............. 601/3 |
| 5,158,536 A | 10/1992 | Sekins et al. |
| 5,179,455 A | 1/1993 | Garlick |
| 5,212,571 A | 5/1993 | Garlock et al. |
| 5,255,683 A | 10/1993 | Monaghan |
| 5,260,871 A | 11/1993 | Goldberg |
| 5,267,566 A | 12/1993 | Choucair et al. |
| 5,269,309 A | 12/1993 | Fort et al. |
| 5,280,788 A | 1/1994 | Janes et al. |
| 5,304,173 A | 4/1994 | Kittrell et al. |
| 5,318,028 A | 6/1994 | Mitchell et al. |
| 5,329,817 A | 7/1994 | Garlick et al. |
| 5,349,954 A | 9/1994 | Tiemann et al. |
| 5,372,138 A | 12/1994 | Crowley et al. |
| 5,413,108 A | 5/1995 | Alfano |
| 5,415,164 A | 5/1995 | Faupel |
| 5,421,338 A | 6/1995 | Crowley et al. |
| 5,433,202 A | 7/1995 | Mitchell et al. |
| 5,463,548 A | 10/1995 | Asada et al. |
| 5,465,722 A | 11/1995 | Fort et al. |
| 5,474,072 A | 12/1995 | Shmulewitz |
| 5,479,927 A | 1/1996 | Shmulewitz |
| 5,485,839 A | 1/1996 | Aida et al. |
| 5,487,387 A | 1/1996 | Trahey et al. |
| 5,492,126 A | 2/1996 | Hennige et al. |
| 5,524,630 A | 6/1996 | Crowley |
| 5,553,618 A | 9/1996 | Suzuki et al. |
| 5,558,092 A | 9/1996 | Unger et al. |
| 5,573,497 A | 11/1996 | Chapelon |
| 5,582,173 A | 12/1996 | Li |
| 5,588,032 A | 12/1996 | Johnson et al. |
| 5,590,653 A | 1/1997 | Aida et al. |
| 5,590,657 A * | 1/1997 | Cain et al. .................. 600/439 |
| 5,596,992 A | 1/1997 | Haaland et al. |
| 5,606,971 A | 3/1997 | Sarvazyan |
| 5,620,479 A | 4/1997 | Diederich |
| 5,640,956 A | 6/1997 | Getzinger et al. |
| 5,643,179 A | 7/1997 | Fujimoto |
| 5,664,573 A | 9/1997 | Shmulewitz |
| 5,678,565 A | 10/1997 | Sarvazyan |
| 5,715,825 A | 2/1998 | Crowley |
| 5,722,411 A | 3/1998 | Suzuki et al. |
| 5,743,863 A | 4/1998 | Chapelon |
| 5,762,066 A | 6/1998 | Law et al. |
| 5,766,129 A | 6/1998 | Mochizuki |
| 5,785,663 A | 7/1998 | Sarvazyan |
| 5,797,849 A | 8/1998 | Vesely et al. |
| 5,800,350 A | 9/1998 | Coppleson et al. |
| 5,810,731 A | 9/1998 | Sarvazyan et al. |
| 5,817,025 A | 10/1998 | Alekseev et al. |
| 5,830,133 A | 11/1998 | Osten et al. |
| 5,833,614 A | 11/1998 | Dadd et al. |
| 5,833,633 A | 11/1998 | Sarvazyan |
| 5,836,882 A | 11/1998 | Frazin |
| 5,836,894 A | 11/1998 | Sarvazyan et al. |
| 5,846,202 A | 12/1998 | Ramamurthy et al. |
| 5,851,182 A | 12/1998 | Sahadevan |
| 5,865,167 A | 2/1999 | Godik |
| 5,865,743 A | 2/1999 | Godik |
| 5,891,619 A | 4/1999 | Zakim et al. |
| 5,945,674 A | 8/1999 | Dukor |
| 6,002,958 A | 12/1999 | Godik |
| 6,109,270 A | 8/2000 | Mah et al. |
| 6,117,080 A | 9/2000 | Schwartz |
| 6,135,960 A * | 10/2000 | Holmberg .................. 600/447 |
| 6,146,897 A | 11/2000 | Cohenford et al. |
| 6,165,734 A | 12/2000 | Garini et al. |
| 6,385,474 B1 * | 5/2002 | Rather et al. ............... 600/407 |
| 6,428,477 B1 * | 8/2002 | Mason ........................ 600/437 |
| 6,451,013 B1 * | 9/2002 | Bays et al. .................... 606/27 |
| 6,540,678 B2 * | 4/2003 | Rather et al. ............... 600/437 |
| 6,612,988 B2 * | 9/2003 | Maor et al. .................. 600/439 |
| 2001/0051774 A1 * | 12/2001 | Littrup et al. ............... 600/547 |
| 2002/0065466 A1 * | 5/2002 | Rather et al. ............... 600/447 |

FOREIGN PATENT DOCUMENTS

| | | | |
|---|---|---|---|
| EP | 320444 | 6/1989 | |
| EP | 351610 | 1/1990 | |
| EP | 538241 | 4/1993 | |
| EP | 609922 | 1/1994 | |
| EP | 614651 | 9/1994 | |
| EP | 642762 | 3/1995 | |
| EP | 661029 | 7/1995 | |
| EP | 774276 | 5/1997 | |
| WO | WO 99/47046 * | 9/1999 | ............ A61B/8/08 |

* cited by examiner

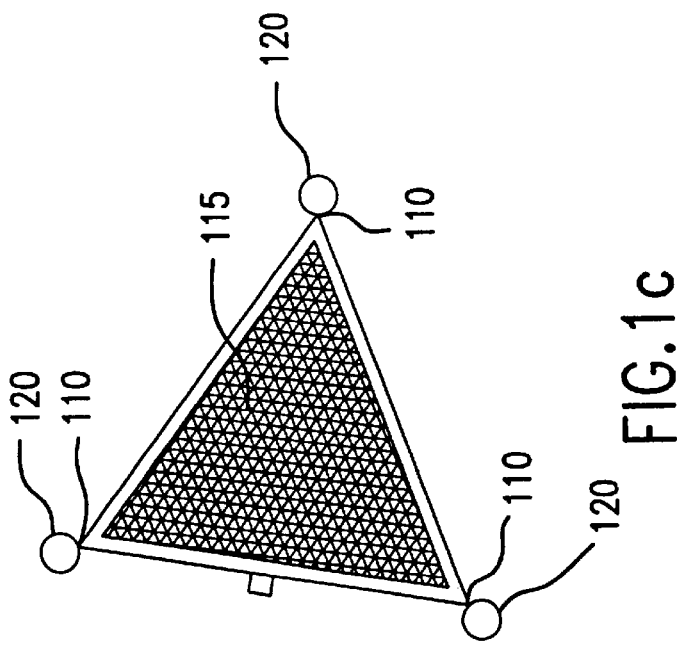
FIG.1c
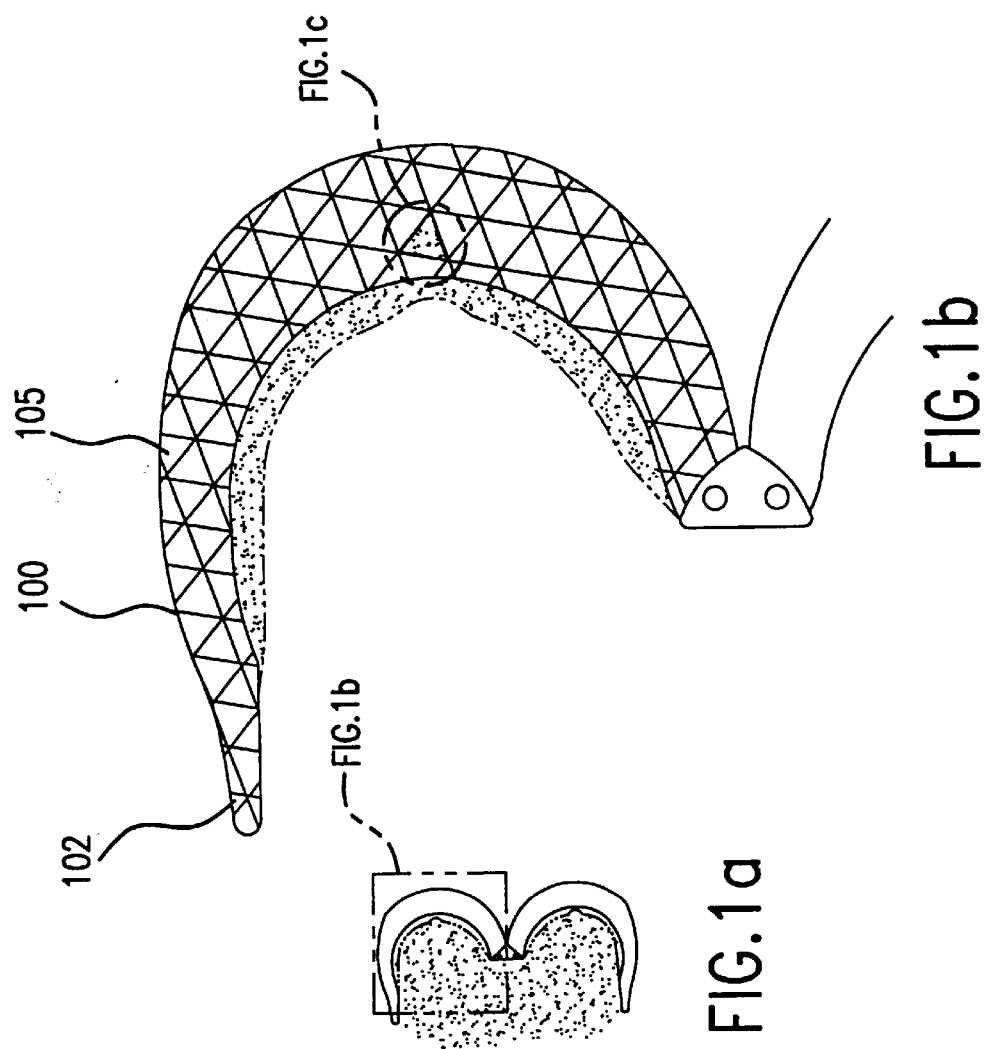
FIG.1b
FIG.1a

1

| 00000 | 00001 | 00011 | 00010 | 00110 | 00111 | 00101 | 0010 |
| --- | --- | --- | --- | --- | --- | --- | --- |
| 01100 | 01101 | 01111 | 01110 | 01010 | 01011 | 01001 | 0100 |
| 11000 | 11001 | 11011 | 11010 | 11110 | 11111 | 11101 | 1110 |
| 10100 | 10101 | 10111 | 10110 | 10010 | 10011 | 10001 | 1000 |

METHOD AND APPARATUS FOR HIGH-RESOLUTION DETECTION AND CHARACTERIZATION OF MEDICAL PATHOLOGIES

This application is a continuation of U.S. patent application Ser. No. 09/272,452 filed Mar. 19, 1999, now U.S. Pat. No. 6,358,474 issued Jul. 5, 2002, and claims priority from Provisional Application 60/078,788 filed Mar. 20, 1998.

FIELD OF THE INVENTION

The present invention relates to the detection and characterization of medical pathologies in human and animal bodies. More particularly, the present invention relates to the detection and identification of cancer in organs or tissues.

BACKGROUND OF THE INVENTION

There are no available systems today, for medical or non-medical applications, to detect and characterize distinct features within an object under study, such as cancerous lesions and tumors in a human body. Presently, only imaging systems are available, such as imaging systems based on x-ray, mammography, computed tomographic (CT) scans, or magnetic resonance imaging (MRI). All of these imaging systems simply provide images of pathologies within a human body; they do not characterize any features.

In addition, each of these imaging technologies has significant drawbacks. For example, x-rays, mammography, and CT scans all use ionizing radiation and therefore present certain health risks to a patient, such as cell mutations. Also, both CT scans and MRI involve procedures that are relatively expensive, which hampers their widespread use. Moreover, both MRI and CT scans require the expertise of highly trained personnel for extended periods of time to operate the devices and to interpret the results. Furthermore, each of these imaging technologies requires that the patient lie still, sometimes for an extended period of time. This restriction on movement may not only inconvenience the patient, but also discards information that could potentially be discovered from the movement of tissues within the patient. As to mammography, it is particularly uncomfortable for the patient since it requires that the breast be compressed to allow more uniform tissue density, better x-ray penetration, and tissue stabilization. More importantly, methods such as mammography rely on two-dimensional images, thus disguising three-dimensional structure information which can be critical for diagnosis.

As an alternative to the above-mentioned imaging technologies, the medical community has looked to ultrasound for providing a safe, low-cost, high-resolution imaging tool. However, conventional ultrasound (ultrasonic B scanning) has certain limitations. In conventional ultrasound analysis, a small array of less than approximately 1000 elements is moved by hand in contact with the object under study. In fact, most current ultrasound arrays have only 256 elements. The array sends out waves that reflect from tissues back to the same array. Trained technicians and physicians are needed to conduct the ultrasound imaging procedure and to interpret the results. This reliance solely on the reflected waves results in two major drawbacks. First, ultrasonic B scans do not provide information on the properties of the materials themselves; rather, they provide information on the reflectivity of the boundaries between different types of materials. Second, the array is incapable of capturing radiation except that which is reflected back to the hand-held sensing array. Considerable information exists, however, in the transmitted waves, which is not captured or used in conventional ultrasonic B scans.

There is thus a need for an apparatus and method that provides detection and characterization of medical pathologies in a human body. More generally, there exists a need to detect and characterize distinct features within an object under study.

SUMMARY OF THE INVENTION

The present invention provides construction and use of multidimensional field renderings for high-resolution detection and characterization of distinct features within a three-dimensional object. More particularly, the invention provides construction of such multidimensional field renderings for high-resolution detection and identification of medical pathologies in human and animal bodies, especially high-resolution detection and identification of cancer in organs or tissues. The present invention also provides detection and characterization of other medical pathologies including pathologies of musculoskeletal systems, digestive systems, and the alimentary canal, in addition to atherosclerosis, arteriosclerosis, atherosclerotic heart disease, myocardial infarction, trauma to arterial or veinal walls, and cardiopulmonary disorders.

The present invention provides construction of a multidimensional field rendering that describes the physical details of any three-dimensional object under study. By correlating the information contained in such a multidimensional field with information regarding known details of general objects under study by using a trained evaluation system, the present invention provides detection and characterization of the structures that exist in the object under study. For example, the present invention provides a system based on ultrasound which, when it is used to observe a human breast, correlates a catalog of known morphologies and acoustic characteristics of tissue types that are known to exist in breast tissue with the multidimensional field derivation of physical properties; then the system of the present invention detects and characterizes various tissues including fibroadenoma, fat, fibroglandular tissue, and benign versus malignant lesions or tumors.

The present invention provides a method and apparatus that allows for the detection and characterization of features within an object under study. The invention uses an array of radiation sources and an array of radiation detectors to collect scattered radiation regarding the object under study. In one preferred embodiment, the source array and detector array are configured as a single integrated unit. In another preferred embodiment, the radiation sources and detectors are the same physical devices; they operate in one time period as radiation emitters and in another time period as detectors. In yet another preferred embodiment of the invention, the arrays comprise large numbers of sources and detectors, referably with more than 5000 detectors. With a sufficient number of such sources and detectors, the present invention provides for construction of a three-dimensional rendering of numerous physical quantities to describe the object and therefrom derive interpretations. The radiation sources emit radiation of a specific waveform, either within a predetermined frequency range or at a predetermined frequency, which is propagated within the object under study and subsequently scattered by features within the object under study. Generalized scattering includes reflection (backscattering), transmission (forward scattering), and diffraction, which may occur in any or all directions from the features within the object under study. All these types of secondary waves constitute the wave signal returned from the object under study.

In a preferred embodiment, the radiation sources and detectors cover a large solid angle, thereby substantially enclosing the object under study. As a result, a large fraction of all these types of secondary waves are detected by the radiation detectors. The resolution depends on the product of the number of sources and the number of detectors, which defines the number of resolution elements into which the volume occupied by the object under study may be divided.

In a preferred embodiment of the invention, the radiation is ultrasound radiation, although the invention generally encompasses the use of any radiation, including electromagnetic and acoustic radiation. In more specific embodiments of the invention, the object under study is tissue or an organ, or other part of an animal body such as the human body. By using a sufficiently large number of detectors and sources, a high resolution multidimensional field is provided in accordance with the present invention. In another embodiment of the present invention, the sources are modulated to have different phases, which permits focusing or scanning of the radiation.

In accordance with another embodiment of the present invention, the radiation is sufficiently focused and is used to destroy features within the object, such as cancerous lesions within human or animal tissue.

In accordance with the present invention, the data collected by the radiation detectors are then used to construct a rendering of a multidimensional field, represented herein as $q[r,t:\Theta(r,t)]$, that represents physical characteristics of the object under study. The vector r represents the position coordinate of a particular volume element ("voxel"); "t" is the time' and "$\Theta$" is a list of the physical parameters associated with the field at that voxel. In general, the field and each physical parameter are both spatially and time dependent. The multidimensional field comprises estimates of the values for this set of parameters that individually represent physical characteristics of the object under study. These parameter values, taken together, characterize the properties of features within the object under study. In the case of medical applications, this characterization results in the identification of focal regions, their probability of pathology, such as malignancy, and associated probabilities of frequency distribution and error rate.

As an illustration, consider those embodiments of the invention where the radiation is ultrasound radiation and the object under study is a human organ. In this illustration, $q[r,t:\Theta(r,t)]$ may describe, for example, the sound speed, sound absorption, tissue pressure, density, shear modulus, elasticity, etc., of the organ as functions of frequency. The field values are stored electronically into a computer-readable medium, such as a floppy disk, random access memory, or hard memory disk. This allows subsequent processing of the stored field values.

In accordance with a preferred embodiment of the present invention, the construction of the rendering of the multidimensional field $q[r,t:\Theta(r,t)]$ from the detected data, which comprise elements from a description of the waveform of the detected radiation at the location of each detector, is accomplished with an optimal signal processing technique.

In one embodiment of the invention, this is accomplished with matched-field processing, in which the field rendering is constructed so as to produce model detector data that matches the actual detector data, and which may be achieved through an iterative technique. In this iterative technique, the shape of the object under study is first estimated. This can be achieved in a number of different ways, using existing techniques, such as using the transmission-only radiation detected and developing the initial estimate with conventional computer tomographic techniques. In the embodiment where the object under study is human or animal tissue, organ, or other body part, this initial estimate is referred to as an "anatomic" construction.

An initial estimate of the multidimensional field $q^{est}[r,t:\Theta(r,t)]$ is then calculated by injecting physiological data to produce a "physiological" construction. This proceeds by using a pattern-recognition algorithm, such as an expert system, to analyze the morphological features of the anatomic construction and thereby to assign an initial, nominal estimate of the multidimensional field. This nominal estimate is based solely on average values that structures in the object are expected to have based on their morphologically based identification by the pattern-recognition algorithm. The pattern-recognition algorithm achieves this initial assignment by comparing the morphological features of the anatomic construction with a database of stored morphological features, such as elongation, flatness, jaggedness, etc.

At this point, the physical characteristics of the object contained in the estimated field $q^{est}[r,t:\Theta(r,t)]$ are input into a wave-propagation code, together with the information concerning the characteristics of the radiation that was initially generated. Such a wave-propagation code can be used to generate the waveform of the radiation that would be expected at the locations of the detectors based on this information. Such wave-propagation codes can be rather complex, but exist in the prior art. Once these signal data have been generated based on the estimated field, they are compared with the actual signal data that was received by the detectors. If the difference between the two sets of signal data is at the level expected for noise in the system, then the estimated field is taken to be the actual constructed field rendering, i.e. $q[r,t:\Theta(r,t)] \equiv q^{est}[r,t:\Theta(r,t)]$.

If, however, the comparison with the actual signal data shows that the difference between the signals generated by the estimated field and the actual signals is greater than the expected noise in the system, then a correction to the estimated field is calculated. This correction is determined by using a wave-propagation code to generate a refinement field $C[r,t:\Theta(r,t)]$ from the difference in actual signals and signals that would be produced by the estimated multidimensional field. This refinement field is then used to modify (e.g., by adding to) the estimated field to produce a new estimated field, which is then used to calculate a new set of detected signals. The process is iterated until the set of signals generated from the estimated multidimensional field $q^{est}[r,t:\Theta(r,t)]$ converge to a converged multidimensional field $q[r,t:\Theta(r,t)]$, which generates waveform signals that are within the noise level of the actual set of detected signals.

Once the multidimensional field $q[r,t:\Theta(r,t)]$ has been calculated, it is interpreted so as to characterize the object under study. This is done, for example, with the use of an expert system, neural net, or other trained evaluation system that has been taught to take the values calculated for $q[r,t:\Theta(r,t)]$ at every voxel and to reach a determination of what the identified features in the object under study are. The specific features of the multidimensional field that are relevant for the interpretation method executed by the trained evaluation system depend both on what the object under study is and on what is to be learned about the object.

For example, in the embodiment of the invention where human or animal tissue or an organ is studied with ultrasonic radiation and the goal is to identify diagnostic parameters suggestive of the existence of cancer, there are at least seven identification methods that are used to extract information from the multidimensional field so as to allow the trained evaluation system to draw such interpretations.

In a first identification method, the converged multidimensional field will contain the sound speed and sound absorption of the tissue or organ at every voxel. The trained evaluation system will then classify the type of tissue present at every voxel based on this information, and will identify cancerous tissue based on these particular physical properties.

In a second identification method, a Hough transformation of the multidimensional field is used to identify closed volumes in the tissue, which are indicative of the existence of neoplasms.

In a third identification method, the existence of angiogenesis and other anomalies of the circulatory system are identified by examining three-dimensional blood flow with the Doppler effect.

In a fourth identification method, the tissue pressure is extracted from the multidimensional field and correlated with the localization of an enclosed volume, as well as any distinct results from the other identification methods.

In a fifth identification method, the Doppler effect is used to analyze the effects of external vibrations on the tissue, which produce characteristic results in the multidimensional field to allow the identification of tissue shear modulus. In a related method, microcalcifications and tissue elasticity, which are also suggestive of cancer, produce a characteristic Doppler signature.

In a sixth identification method, information regarding the electrical impedance of tissue is extracted from the multidimensional field. This information is related to the existence of tumors.

In a seventh identification method, the multidimensional field rendering is constructed at two different times and compared either to study changes over time in the tissue or to allow the use of interferometric techniques to improve the resolution.

The actual identification of medical pathologies such as cancerous tissue preferably uses more than one of these identification methods in conjunction. With the use of multiple identification methods, the reliability of the evaluation is improved. In this way, for example, a human breast may be examined with ultrasonic radiation to identify cancerous tissue at the desired resolution. In other embodiments, the invention is used to identify cancer in other organs, such as the prostate, colon, lung, etc.

OBJECTS AND ADVANTAGES OF THE INVENTION

It is thus an object of the invention to produce an apparatus and method for sensing the spatial, or spatial and temporal, properties and determining the physical and/or biological nature of materials in a substantially enclosed volume.

It is another object of the invention to perform sensing operations that uniquely identify physical properties in contiguous, highly resolved volume elements throughout the sensed media.

It is yet another object of the invention to provide a disease-detection system specifically designed to find small, subtle indicators of early pathology, including cancer, vascular disease, etc.

It is still a further object of the invention to produce a class of physics-based diagnostic devices that probe the subject environment, observe the response of the contents to the probing disturbance, and then diagnose the implications of the measured data.

An advantage of the invention is that it provides detection and identification of tissue anomalies where the object under study is animal or human tissue or an organ. In particular, the invention detects and identifies cancerous tissue in animal and human organs. The invention also provides detection and identification of other medical pathologies in systems including cardiovascular, musculoskeletal, or digestive systems. The disease states that may be characterized include trauma, infection, neoplasms, and disorders of various biochemical pathways.

It is a further advantage of the invention that it provides construction of the multidimensional field rendering in three spatial dimensions by using of all scattered radiation, which includes radiation reflected, transmitted or diffracted by the object under study or by features within the object under study.

An additional advantage of the invention is that it permits the complete use of Doppler shifted data, since there is no limitation to Doppler shifts that lie in a single plane of examination.

Other objects and advantages may occur to those of skill in the art after reading the detailed disclosure and figures. The invention is not limited to those objects and advantages recited above, but encompasses all objects and advantages that would occur to those of skill in the art in light of the disclosure.

BRIEF DESCRIPTION OF THE DRAWINGS

FIG. 1(a) and FIG. 1(b) show cross-sectional views of the detection and identification apparatus for one embodiment of the invention with a geodesic dome configuration, which is a geometrical construction appropriate for investigation of the human breast.

FIG. 1(c) is a plan view of one embodiment of the radiation source and detector arrays.

FIG. 4 is an example of a modulation sequence of the radiation sources and detectors using Walsh Function modulation.

DETAILED DESCRIPTION OF THE INVENTION

Figure 2:
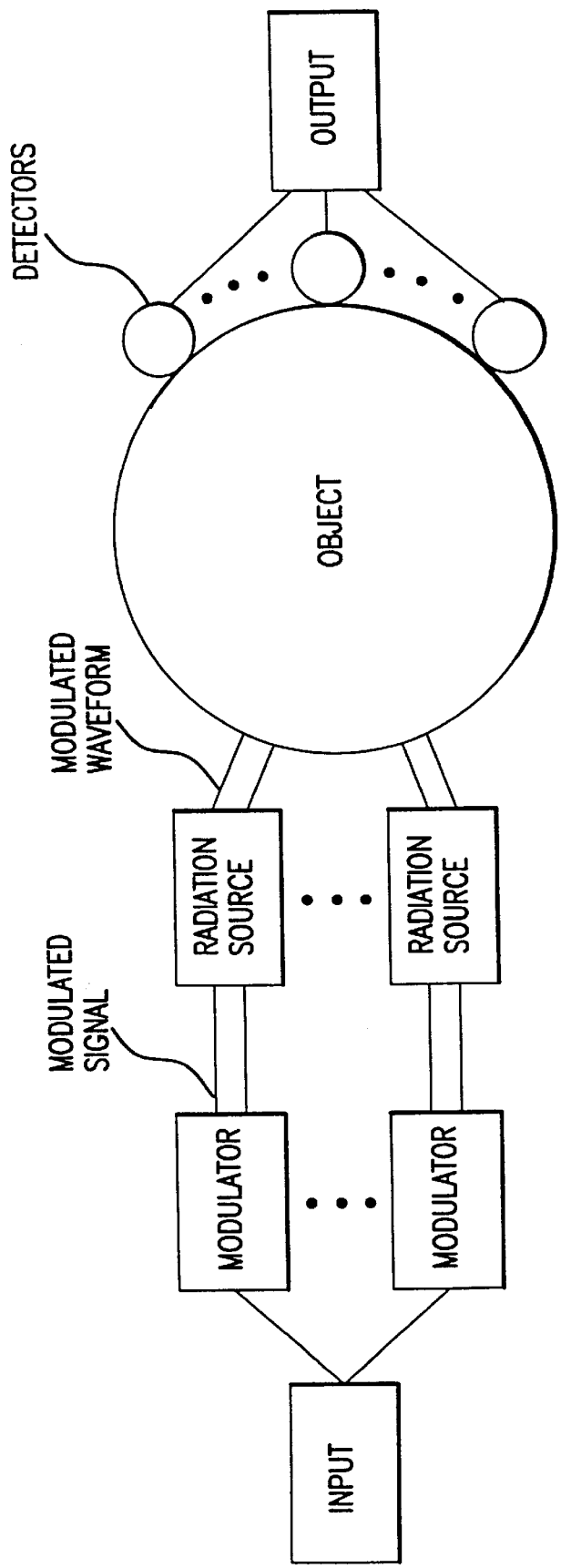
FIG. 2 is a block diagram of an arrangement of the radiation sources and detectors in one embodiment of the invention.

The invention is described in detail in the following. Although reference is sometimes made to a specific embodiment of the invention wherein the radiation that is used is ultrasound radiation, it will be appreciated by those of skill in the art that the invention is not so limited. The invention encompasses the use of any type of radiation, including both acoustic and electromagnetic radiation, and reference to the specific embodiment of ultrasound radiation is not intended to be limiting. Reference is also made in the following detailed description to application of the method on a human patient to diagnose cancer. Such reference is again not intended to be limiting and represents only a preferred embodiment of the invention.

The invention relates both to an apparatus and a method that can be used to allow the detection and characterization of features within an object under study. The invention achieves this detection and characterization by constructing a rendering of a multidimensional field $q[r,t:\Theta(r,t)]$ at every volume element ("voxel") that can be resolved. Here, r represents the position coordinate of a voxel, and $\Theta$ is a list of the physical parameters that are associated with the field at that voxel. In principle, $q[r,t:\Theta(r,t)]$ can include information on whatever physical properties are desired for the application of interest. On perhaps the simplest level, the multidimensional field $q[r,t:\Theta(r,t)]$ may contain information for construction of a visual image of the object under study. For some applications, however, it is more useful for $q[r,t:\Theta(r,t)]$ to be constructed to describe other, more relevant physical properties of the object.

The versatility of the general multidimensional field $q[r,t:\Theta(r,t)]$ may be illustrated with an example of one embodiment of the invention, where the object under study is a human breast, the goal of studying the object is to identify cancerous tumors, and ultrasound radiation is used. If all that is desired is an image of the breast, showing its internal structures, then $q[r,t:\Theta(r,t)]$ can be constructed as a one-dimensional scalar field that contains a single quantity, such as the density, of the object at every point, i.e. $\Theta=\{\rho\}$. The detection and/or identification of tumors is, however, more readily accomplished by an examination of quantities such as the sound velocity, sound absorption, and tissue pressure. In this case, $q[r,t:\Theta(r,t)]$ can be constructed as a field containing the values of these quantities at every voxel, i.e. $\Theta=\{v, A, P\}$, where v is the sound velocity, A is the sound absorption, and P is the tissue pressure.

1. Apparatus

In order to generate the radiation that is used in the invention, there must exist radiation sources. Although it is within the scope of the invention to use a single radiation source, it is preferred that there be multiple sources of the radiation. In instances where a single radiation source is used, collection of sufficient appropriate data to construct the multidimensional field rendering of the object under study may require that the source be large and/or in motion. In general, the sources are configured so as to minimize the volume of the object under study that is not reached by radiation emitted from the sources. The radiation sources are adapted to emit radiation within a predetermined frequency range or at a predetermined frequency. In the embodiment where the sources provide ultrasound radiation, the sources are arranged so that there are few or no uninsonified regions in the volume of interest.

In those embodiments of the invention where there are a multiplicity of radiation sources, the sources can be arranged in a wide variety of geometric configurations. These different configurations allow for the measurement of properties of differently shaped objects. In particular, these different configurations allow for the achievement of one objective of the invention, which is to provide a large solid angle $\Omega$ over which the object is studied. This is desirable in order to obtain the greatest level of information possible by substantially enclosing the object under study. Preferably, the coverage of the apparatus is $\Omega \geq 2\pi$ sr.

Illustrations of such configurations can be made for the study of certain anatomical features of human beings, which is one embodiment of the invention. For example, where the object under study is a human breast, a modified hemispherical arrangement of radiation sources will provide large coverage ($\Omega \approx 2\pi$). If the object under study is a human limb, then a cylindrical arrangement can provide $\Omega > 2\pi$. Alternative arrangements include the use of concentric cylinders, or portions of concentric cylinders, where the object under study is an organ inside the human body, and this can also provide a sufficient solid angle with $\Omega > 2\pi$. In one example, a small internal cylinder is inserted into the alimentary canal of the patient, and a larger external cylinder or cylindrical arc is positioned outside the patient near the object under study. In this manner, for example, the requisite large solid angle coverage is achieved when analyzing the human prostate. Other array configurations include ellipsoids as well as cones and truncated cones.

It will be readily appreciated that these are merely examples of the types of configurations that can be made for different objects under study. It is also within the scope of the invention to combine these examples to create additional configurations adapted to other objects, and the invention is not limited by the configuration. For example, in the case of study of the human breast, it is preferable to have additional coverage beyond a hemisphere, such as the geodesic-dome configuration that is shown in FIG. 1(b), because tumors frequently manifest themselves in the upper outer quadrant going towards the axilla and in the axillary lymph nodes (under the arms). In other embodiments of the invention, an appropriate configuration is used to detect and identify cancers in other parts of the body, such as the prostate, liver, lung, or portion of the alimentary canal.

In one embodiment of the invention, the sources emit radiation that is uniform in phase, although in alternative embodiments, the phase of the radiation emitted by each source may be varied. This is achieved by individual encoding of each individual source as described below. This variation of phase may be structured so as to focus the radiation in particular areas of the object under study or it may be structured so as to scan the entire object under study. In cases where the phase variation is structured so as to focus narrowly, it allows the possibility of confocal microscopy of the object under study. Furthermore, if the radiation is sufficiently focused, it may be of an intensity that can be used to destroy well-defined features within the object under study if this is a desired objective for the particular application of the invention. For example, the focused radiation could be used to destroy cancerous tissue discovered in an organ without invasion of the body by a surgical instrument.

The invention also comprises a multiplicity of radiation detectors. These detectors are also placed so as to cover a large solid angle, again preferably greater than $2\pi$ sr, and can be arranged in the same types of geometric patterns that were described above in relation to the sources to achieve this coverage. In most applications, the geometric pattern used for the detectors will be similar to the geometric pattern used for the sources, but the invention is not so limited. The invention also encompasses embodiments where the number of detectors greatly exceeds the number of radiation sources.

It will readily be appreciated by those of skill in the art that the spatial resolution of the device is directly related to the number of sources and detectors that are used, as well as to the frequency of the radiation. The product of the number of sources and the number of detectors should be at least as large as the number of voxels needed to achieve the desired resolution. Although there is no fixed limit on the number of sources and detectors, provided the appropriate number are used to achieve the desired resolution, the invention encompasses the use of considerably more detectors than used in the prior art. The resolution is governed principally by the Nyquist criterion, which states in its simplest form that in order to prevent undesired aliasing, one must sample a signal spatially at least twice in a wavelength. Thus, full sampling of the object under study is achieved by placing detectors closely spaced at the Nyquist half-wavelength limit, as dictated by the frequency of the radiation to be used.

In embodiments of the invention applied to the identification of cancer in tissue, for example, it is preferred that the resolution be sufficient to detect small neoplastic masses with diameters less than 3 mm. In the case of identification of cancer in the human breast, an embodiment of the invention uses approximately 250 ultrasound sources and approximately 4,000,000 ultrasound detectors. At an operating frequency of 5 MHZ, this would achieve a resolution of approximately 0.3 mm for a hemisphere with a diameter of 20 cm, corresponding to the volume occupied by a breast. In other embodiments of the invention, the frequency of the radiation and the required resolution may dictate a need for considerably fewer sources and detectors, or for very detailed studies could require even greater numbers of sources and detectors.

In different embodiments of the invention, the detectors can measure either the longitudinal or transverse waves ("shear waves" in the particular case of ultrasound), or, preferably, both the longitudinal and transverse waves. Different embodiments also correspond to which components of the waveform are measured by the detectors. In particular, the amplitude, phase, and/or frequency of the detected waves is/are measured, although it is preferable that all three be measured since this provides more information that can be used to construct the rendering of the physical multidimensional field $q[r,t:\Theta(r,t)]$. It is also preferable that the detectors be configured so as to detect both waves that have been reflected from the object under study and transmitted through the object under study. Again, this is preferred so as to extract as much information as possible from the detected radiation, and such configurations are more readily achieved when the arrays of sources and detectors are arranged so that the solid angle $\Omega \geq 2\pi$.

Referring to FIG. 2, there is shown a detailed block diagram of a preferred arrangement of the radiation sources and corresponding detectors. A master controller ("Input") generates the modulation strategy and a master detector ("Output") controls what comes out of the detectors. A modulator coupled to a radiation source generates a modulating signal. The radiation source, in turn, generates a modulated waveform signal based on the modulating signal received from the modulator. Each modulator generates a distinctive modulating signal, thereby causing each radiation source to generate a distinctive modulated waveform signal. It should be noted that one modulator may be coupled to a plurality of radiation sources generating a plurality of distinctive modulating signals for the coupled radiation sources.

There exist many digital coding methods and designs for modulating waveforms for the purpose of encoding waves, depending upon the desired correlation properties. See generally K. Sam Shamugam, *Digital and Analog Communication Systems* (John Wiley & Sons, New York, 1979), which is herein incorporated by reference. Two examples of digital switching modulation schemes are given here. Linear maximal length (LML) codes have excellent autocorrelation for time resolution, and the Walsh functions (WF) have superior cross-correlation for spatial resolution. An encoding scheme is provided for each. The waveform signals generated from the sources are transmitted, reflected or refracted though the object and arrive at a plurality of detectors. Each detector includes at least one matched filter designed to decode one distinctive modulated signal. If the emphasis is to be placed on temporal resolution, coding sequences such as LML codes may be used for modulation. Alternatively, if the emphasis is on spatial resolution, then orthogonal sequences such as Walsh sequences may be used. An example of the radiation source-detector design scheme for each type is detailed in the following descriptions.

Figure 3:
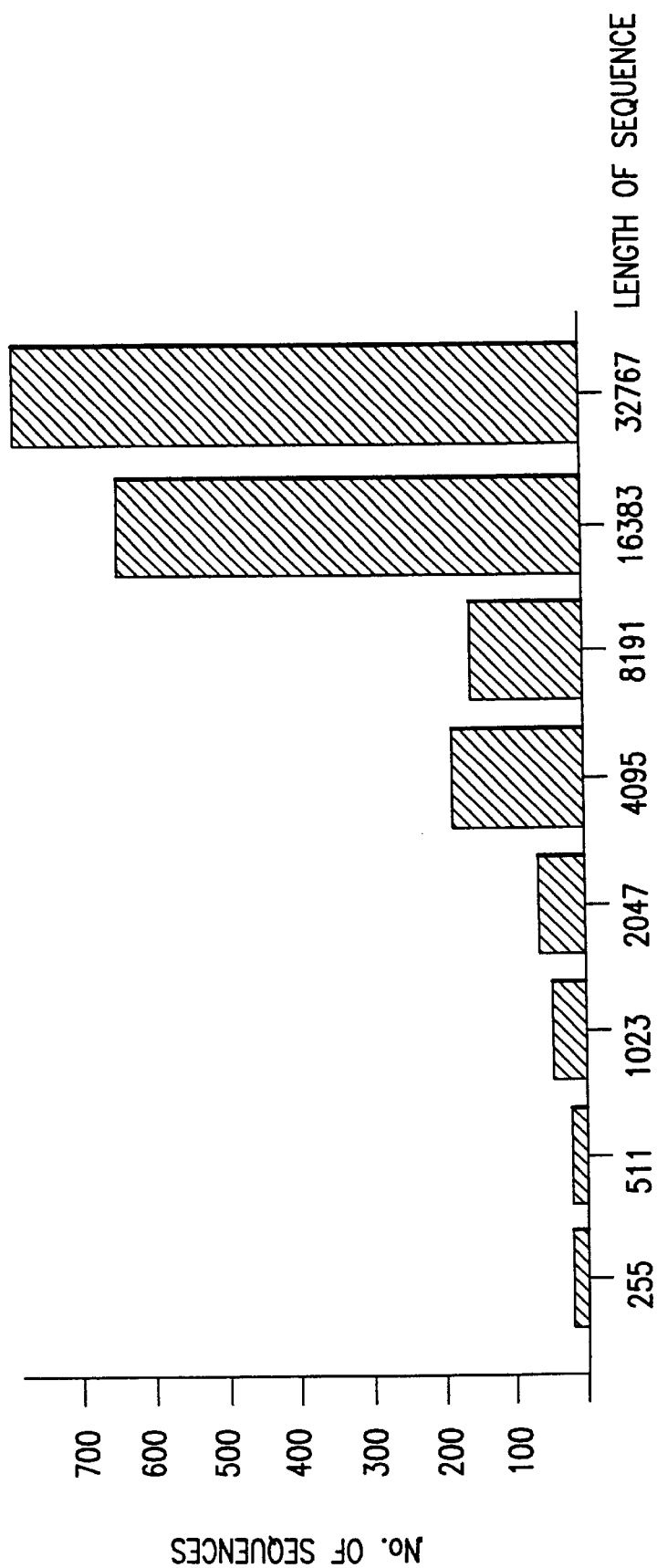
FIG. 3 is a histogram that illustrates the relationship between the number of sequences and the sequence length in the use of linear maximal length sequence modulation of the radiation sources and detectors.

Using the LML sequence modulation, described, for example, in K. Metzger, Jr. and R. J. Bouwens, *An Ordered Table of Primitive Polynomials Over GF[2] of Degree 2 to 19 for Use with Linear Maximal Sequence Generators*, Cooley Electronics Laboratory, University of Michigan Tech. Memo No. 107 (1972), which is herein incorporated by reference, each sequence of modulated signals is generated by means of a multiple stage digital shift register with a feedback mechanism, based on a primitive polynomial of degree N, where N is a positive integer. The length of the sequence is related to the degree of the polynomial, which determines the number of distinct sequences that can be generated. The relationship between the number of distinct sequences and the length of sequence is depicted in FIG. 3. For instance, for a sequence length of 2047, the number of available distinct sequences is 60. Therefore, for a scheme where its sequence length is 2047, it is possible to generate 60 distinct waveform signals from 60 radiation sources.

The modulating signals from the modulators are input to the radiation sources. Upon receiving the modulating signals, the radiation source preferably shifts phases of its carrier waveform in accordance with the modulating signals. In alternative embodiments, the amplitude or frequency of the carrier waveform can be changed based on the modulating signals. The carrier waveforms are then emitted from the radiation sources and scattered, transmitted, reflected or refracted by various internal parts within the object. Eventually, the waveforms arrive at the detectors.

Each detector includes at least one matching filter capable of decoding the arrived waveform signals. In other words, a matching filter is provided to decode each distinct sequence identifying the individual radiation source. Therefore, knowing the locations of the radiation sources and the locations of the detectors, the path through which the waveforms traveled can be estimated. Further, using the phase shifts, speed changes, amplitude changes and other information extracted from the decoded waveform signals by comparing against the original waveform signals allow internal structures of the object to be characterized.

In another embodiment, if more than 60 radiation sources are required to cover the object at a desired resolution, the repetitive sequences can be reduced to increase the resolution. For instance, if 240 radiation sources are required, then four groups of 60 radiation sources can be cycled on and off reducing corresponding repetitive sequence to 16 but increasing the resolution.

In an alternative embodiment, instead of the LML sequence modulation described above, the Walsh Function (WF) modulation scheme, described, for example, in H. Harmuth, *Sequency Theory: Foundations and Applications, Advances in Electronics and Electron Physics* (Academic Press, 1977), which is herein incorporated by reference, is utilized to generated the modulating signals. The WF modulation takes on the values +1 and −1 but may be linearly transformed to assume digital values of 1 and 0 and then transformed back to their original form for analysis.

The WF modulation is also implemented with a set of shift registers with feedback. The WF modulation also has a sequence length of integer N, but there are many sequences for any value of N compared with the LML sequence modulation. Thus more transmitters may be accommodated by the WF modulation than that of the LML sequence modulation. This characteristic of WF modulation allows for design techniques such as a subsampling of the WF modulation signals to select the most desirable in them of on-off ratios and etc. The WF modulations also have a short length N. Thus they are used in periodic sequences, usually with many repetitions for each pulse. An exemplary WF modulation sequence with 32 possible modulation sequences with length of 5 is illustrated in FIG. 4.

There are a number of specific detectors that may be used in different embodiments of the invention. For example, the detector array may be constructed of silicon micro-electro-mechanical systems (MEMS) detectors, piezoelectric detectors, or deformable dielectric detectors, similar to liquid-crystal arrays. The detector array may alternatively be constructed with PVDF receiver arrays responding to a powerful piezoelectric transmitter. The conventional array that is presently used in ultrasound medicine is made of piezoelectric emitters, which also serve as detectors.

In different embodiments of the invention, the detectors may be integrated into a micro-electro-mechanical chip that contains one or more sensors. The chip itself may contain signal processing elements. In one alternative embodiment of the invention, the radiation sources and detectors exist as a single integrated unit. This is realized, for example, with the use of PZT elements, which can both emit and receive ultrasonic radiation. An example of a separate embodiment where the radiation sources and detectors are individually separate elements, but constructed as a single unit, is provided in FIG. 1(c). In this example, referring to parts (a), (b), and (c) of the figure, the apparatus has been configured for examination of the human breast. As shown in a cross-sectional view in FIG. 1(b), a housing 100 is shaped in a modified hemispherical form. In particular, there are extensions 102 beyond the hemisphere 100 that will protrude onto the side of the patient's torso so as to acquire information including the sides of the chest wall under the arms. The housing 100 is divided into a plurality of segments 105. Each segment 105 may comprise a silicon chip having a plurality of endpoints 110 and a region 115 disposed between the endpoints 110. In the illustrated embodiment, each segment 105 is triangular in shape, with a length of 2 cm per side; each segment 105 has a wave source 120 at each endpoint 110 of the triangle, and each region 115 disposed between the endpoints 110 has 20,000 detectors, each 0.1 mm per side. The segments 105 are used to form the housing 100 in the form of a geodesic dome.

The detector elements themselves may comprise microaccelerometers that are capable of measuring pressure waves by detecting a change in force as a function of time. Alternatively, each detector may comprise a capacitive element having one plate floating on a deformable dielectric medium. As the waves arrive at the detectors after scattering off of and through the object under study, they will cause movement of one of the capacitive plates, causing a change in potential. Another alternative is the use of piezoelectric materials that produce electric signals when mechanically deformed.

The invention may also include a contact to match the impedance between the object to be studied and the arrangement of detectors and sources. Where ultrasound radiation is used, ultrasonic contact with the object under study can be provided in one embodiment of the invention by placing a liquid or gel in contact with the object. In another embodiment of the invention, the entire object under study may be immersed in water, which provides a matched-impedance ultrasonic contact. In yet another embodiment of the invention, the liquid or gel is placed inside a thin membrane; where the object under study is a human organ, this embodiment has the advantage that the patient does not get wet or greasy from the procedure. In a further embodiment, the matched-impedance contact is provided by a plurality of individual contact elements that adapt to the contour of the skin surface and extend from each source and detector to a thin low-impedance deformable membrane that clings to the object under study. This embodiment of the invention is advantageous because it allows for interstitial spaces between the plurality of contacts into which biopsy and other probes may be inserted without interfering with the operation of the apparatus.

There are, additionally, a number of improvements to the apparatus that remain within the scope of the invention. For example, in one embodiment of the invention a mechanism as used to agitate the object under study. This may be done in one embodiment of the invention by applying a vibration source to the body that vibrates at low frequencies, i.e. less than 500 Hz. This agitation causes motion of features within the object under study so that the Doppler effect can be used as an additional means to obtain data such as frequency shifts. If such frequency-shift Doppler data are to be collected and used, it is necessary as an alternative embodiment of the invention that the detectors detect the frequency of received radiation, in addition to the phase and amplitude. These additional data can then be incorporated into the multidimensional field rendering that is constructed, thereby providing a better opportunity to characterize the object under study. In particular, the Doppler effect is useful in this context because microcalcifications in tissue produce well-defined high contrast with the surrounding tissue when external vibrations are applied. This is described in C. M. Sehgal et al., *Visualization of Breast Calcification by Acoustic Resonance Imaging, Radiology Supplement*, 1150 (1999), which is herein incorporated by reference. Near vibration resonance frequencies of 70–250 Hz, the Doppler signal for such microcalcifications is 5–6 times greater than for surrounding tissue, permitting good discrimination of such features. Microcalcifications have also been detectable by Doppler shifting without using vibration. This is described in detail for particles having the size of many breast calcifications in Chelfouh N. et al., *Characterization of urinary calculi: in vitro study of "twinkling artifact" revealed by color-flow sonography, AJR Am. J. Roentgenol.* 171(4):1055–60 (1998), which is herein incorporated by reference. The use of further vibration resonance frequencies may invest a further improvement in the detection and/or characterization afforded by the "twinkling artifact."

The use of the Doppler effect is not restricted, however, to instances where the object under study has deliberately been agitated in order to produce motion. In that case, a coherent vibration is established and construction of the multidimensional field will require an examination for collective motion of adjacent voxels. There are objects, however, in which there is natural motion within the object itself of certain features. This is, for example, the case in the particular embodiment of the invention where the object under study is a human organ such as the breast. Here, there is natural fluid motion of blood through vessels and the identification of this blood flow is useful in the identification of cancerous tumors. The full three-dimensional velocity field shows the enclosing nature of angiogenesis surrounding the tumor. The Doppler effect can thus be used in this embodiment to characterize the vascularization of tissues. The improved agitation discussed above may also induce collective motions of fluids as in, for example, the ducts of the breast.

It will be understood by those of skill in the art that the Doppler effect is dependent on the direction of motion. The aspects of the present invention directed at a field construction in three dimensions, coupled with large solid angle coverage of the object under study, therefore make the present invention highly advantageous over traditional two-dimensional imaging techniques. This is because such two-dimensional techniques are unable to use Doppler information for any component of motion orthogonal to the two-dimensional imaging plane. A three-dimensional Doppler characterization of an enclosed volume may thus produce better volumetric depiction of surrounding vasculature, as well as improved localization of microcalcifications by either "twinkling artifact" or by vibration-induced acoustic resonance imaging.

In another embodiment of the invention, the rendering of the multidimensional field $q[r,t:\Theta(r,t)]$ is constructed for the entire body of a patient. In this so-called "wet suit" embodiment, a suit shaped in the form of a human body, much like a SCUBA suit, is lined with water or another low-impedance material, and radiation sources and detectors are positioned throughout the wet suit. In this embodiment, the object under study may be the entire human body, although such an arrangement may also be used to study isolated parts of the human body, and large solid angle coverage of the body is achieved with an array of sources and detectors that effectively covers the entirety of the body.

As will be evident to one of skill in the art, it is necessary that the arrays of sources and detectors be controlled so as to provide the requisite incident radiation and collect the appropriate data needed to construct the multidimensional field rendering, as well as to generate conclusions that can be drawn from the multidimensional field. This can be achieved with a computer that is suitably programmed. This computer may be used not only to control the timing, amplitude, frequency, and phase of radiation emitted by the sources, but also used to run the field-construction and cancer-detection algorithms described below. Alternatively, separate computers may be used for the control of the sources and detectors and for the field-construction and cancer-detection algorithms. Construction of the multidimensional field $q[r,t:\eta(r,t)]$ is computationally intensive. Thus, a variety of stand-alone processors, such as a parallel processor, an application-specific integrated circuit (ASIC), or a digital signal processing (DSP) chip, to perform the necessary calculations are suitable. In other embodiments, distributed processors, such as dial-up services, or university or other institutional intranet hookups may be used.

2. Construction of the Multidimensional Field $q[r,t:\Theta(r,t)]$

In order to detect and identify three-dimensional features in an object, such as pathologies in tissues, particularly cancer, from the measurements of transmitted and reflected wave signals received by the array of detectors, it is first necessary to construct a rendering of the multidimensional field $q[r,t:\Theta(r,t)]$ from the collected data. Several methods for constructing the multidimensional field rendering are described below, and a particular iterative algorithm is described in detail. While the description below refers to a particular embodiment wherein the detected wave signals are ultrasonic wave signals, it will readily be appreciated by those of skill in the art that the method is more generally applicable to detected radiation of any type, including acoustic and electromagnetic radiation.

Figure 5:
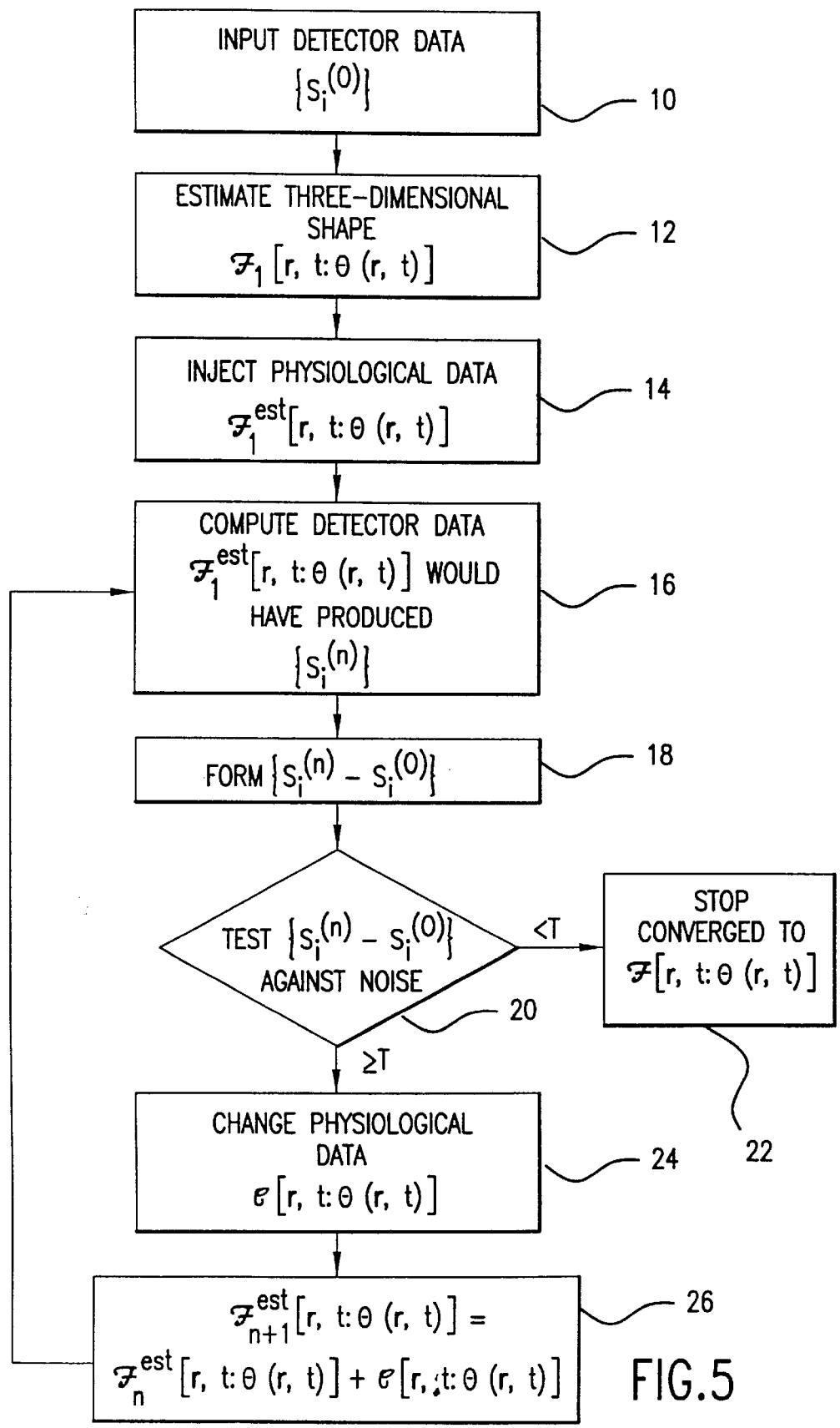
FIG. 5 is a flowchart illustrating a method for constructing the rendering of the multidimensional field $q[r,t:\Theta(r,t)]$ from the data collected by the radiation detectors.

In this method, the objective is to construct a rendering of a multidimensional field $q[r,t:\Theta(r,t)]$, where $\Theta$ is the set of physical properties that will satisfactorily account for the data that have been received by the detectors. The method is displayed in flowchart form in FIG. 5. The initial step 10 is to collect the data from the detectors. This set of data is represented by the set $\{S_i^{(O)}\}$ and contains the amplitude and/or phase of the detected waves, depending on the embodiment of the invention, for every point i where a detector is present in the array. In a specific alternative embodiment, the data also include the frequency of the radiation at every point i where a detector is present; these data can then be used in the construction of $q[r,t:\Theta(r,t)]$ by using information concerning the Doppler shift of radiation as it is scattered off portions of the object in which there is motion. This motion can arise from the natural motion of features within the object, such as the movement of blood in an organ, or can arise from the purposeful agitation of the object by such methods as applying vibration sources directly to the object, as was described above. By collecting data regarding frequency shifts, the Doppler shift data are used to include the velocity of features in the object under study as one of the parameters denoted by $\Theta$ for the multidimensional field.

The second step 12 in the method of analyzing the generated data is to formulate an initial estimate $q[r,t:\Theta_0(r,t)]$ of the multidimensional field that would produce the observed data. In performing this step of the method, it is possible to rely on reconstruction techniques that merely provide a representation of the three-dimensional shape of the object under study, including the shape of internal features. This is preferably done by generating a spatial representation of a single physical quantity, $\Theta_0$, of the object. For example, although this invention ultimately makes use of both the reflected and transmitted waves in the analysis, it is possible to rely solely on transmitted waves to generate the initial estimate of the shape, such as by using standard computerized tomography techniques. Moreover, this initial shape estimate may be made by assuming that the path of the radiation through the object has been along straight-ray paths. While this is certainly not completely accurate for cases such as ultrasound propagation through the human breast because the path of the wave is affected by breast structure, it is a reasonable approximation for the initial shape estimate. This can be performed at low-frequency with decreased resolution. The low-frequency solution can then be integrated in one embodiment of the invention as the frequency is stepped to higher frequency, thus achieving the desired resolution.

With these assumptions, the information that is received by the detectors can be described as the integral of the sound speed and sound attenuation along the straight-ray path taken by the radiation wave. The straight-ray path is that path that would be taken by the radiation wave with no reflection, scattering, or diffraction by the object under study. If this information is collected for each radiation source, then there is sufficient information to permit solving the resulting system of simultaneous equations. See, for example, Gabor T. Herman, *Image Reconstruction from Projections: The Fundamentals of Computerized Tomography* (Computer Science and Applied Mathematics), which is herein incorporated by reference.

Different embodiments of the invention may include additional steps in forming the initial shape estimate $q[r,t:\Theta_0(r,t)]$, such as using image-processing techniques to smooth the shape estimate or to introduce edge completion. Conventional image-processing techniques are described for example, in John C. Russ, *The Image Processing Handbook, Third Edition* (1998), which is herein incorporated by reference. In conventional image processing where an image is dependent on two spatial dimensions, smoothing is accomplished by having a moving window (e.g. 3×3) operate on a given image to calculate an average of pixel values within the window. The pixel value of the moving window is replaced with the average value. This is then repeated for the entire image, thereby smoothing the image. In one embodiment of the invention, an analogous method is used to smooth the initial shape estimate $q[r,t:\Theta_0(r,t)]$, which is instead dependent on three spatial dimensions. In that case, the shape is smoothed by having a moving box (e.g. 3×3×3) that calculates an average over voxels, replacing the voxel value of the moving window with the average value. These methods are especially useful when images contain speckles, but care should be used because there is a tendency to lose information if there is too much smoothing.

In another embodiment of the invention, edges of the initial shape estimate $q[r,t:\Theta_0(r,t)]$ are completed. Conventional edge-completion methods operate by extracting a gradient from the image by computing the difference between neighboring pixels, and thresholding the gradient. Specifically, if the change is greater than a certain value, then that location is designated as the edge. The same principle can readily be applied to detect edges in the initial shape estimate $q[r,t:\Theta_0(r,t)]$. In this case, gradients are extracted from neighboring voxels and if the change is greater than a certain value, then the location is designated as an edge.

Often, edges detected by edge-detection algorithms fail to form closed boundaries. These edges are connected to form continuous boundaries by conventional methods. The conventional methods that are applied when the image is dependent on two spatial dimensions include first grouping edges that touch each other and then growing from that initial group to include edges found to be along the same direction by a few pixels from the initial group, and so on. An analogous method can be applied to complete edges of the initial shape estimate $q[r,t:\Theta_0(r,t)]$, which is dependent on three spatial dimensions. In this case, surfaces that touch each other are initially grouped. From this initial group are progressively grown surfaces that extend in the same direction by a small number of voxels from the initial group. The introduction of edge completion by adapting these existing image-processing techniques is useful because the features of edge detection are relevant to the proper identification of the malignant properties of a mass. This is discussed below in greater detail below with respect to the steps that can be included in identifying cancerous tissue.

At this point in the method, the multidimensional field $q[r,t:\Theta(r,t)]$ has been estimated solely on the basis of the observed waveforms of the detected signals, and contains a representation of the shape of the object and any features within the object; it is therefore described as an "anatomical" estimate of the object under study.

Figure 6:
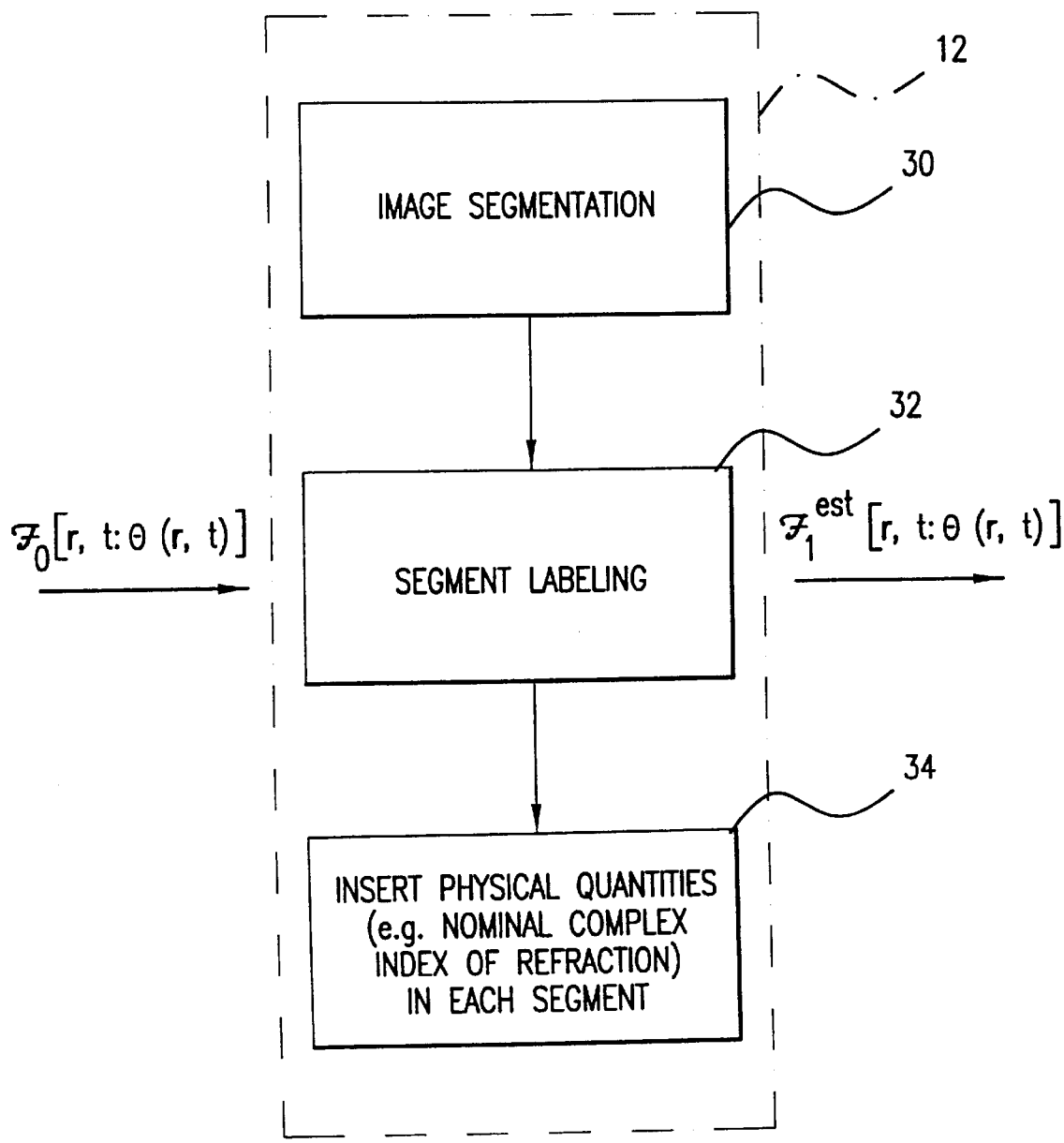
FIG. 6 is a flowchart illustrating in detail a method for injecting physiological data into the initial construction of rendering of the multidimensional field $q[r,t:\Theta(r,t)]$ based on the morphological characteristics of object under study.

The third step in the method 14 is to inject physiological data, so as to refine the estimate and make it more realistic as a "physiological" representation of the object under study. Details of this step are represented in flowchart form in FIG. 6. The first substep 30 in injecting physiological data is to segment the field according to its three-dimensional structure in physical space.

In order to segment the initial three-dimensional shape estimate $q[r,t:\Theta_0(r,t)]$ into separate physical regions, it is necessary to examine the physical quantity $\Theta_0$ that is used to represent the shape, particularly to ascertain where there are abrupt changes in $\Theta_0$. Initially, separate regions are defined according to a criterion such as whether the quantity is high or low. This is done for each individual voxel that exists in the physical space occupied by the object.

It will be understood that once the full set of voxels is designated with such regions, the individual voxels may then be aggregated into segments. For example, if ten neighboring voxels are designated as one region, then the ten voxels should be grouped into a single segment. In this aggregation step, regions are also merged and split appropriately. Thus, for instance, if one voxel is designated as one region, 100 voxels are designated as the same region, but one intermediate voxel is designated as a different region, all 102 voxels should nonetheless be aggregated into a single segment. After this segmentation has been completed, the initial shape estimate $q[r,t:\Theta_0(r,t)]$ will be defined into separate physical regions that have individually defined shapes.

This is then followed by substep 32 of labeling the individual segments. This labeling can be achieved by using a trained evaluation system, such as an expert system or neural network, that relies on stored knowledge of the structures expected in the object under study. One aspect of this labeling may involve the use of a morphological identification database that the trained evaluation system relies upon, the generation of which is described below. For example, in the embodiment whereby cancer is identified in breast tissue, the expert system will have stored the three-dimensional morphological features of the expected structures that exist in the breast. The morphological identification database may define structures according to whether they are elongated, flat, jagged, etc. By examining the morphology of each segmented image and comparing it to the stored catalog of structures in the morphological identification database, the expert system will assign a label to each isolated segment of the field that corresponds to that structure. This morphological database is generated on the basis of analyzing a population, although in alternative embodiments the database is generated for a specific individual.

This labeling of the individual segments, substep 32, is essentially a pattern-recognition algorithm where the trained evaluation system is used to identify the segmented field based on stored morphological data. In any specific implementation of this pattern-recognition algorithm, it is necessary to ensure that the trained evaluation system is making reliable assignments. This is done by preliminary training of the evaluation system with an appropriate set of certifiable data that accounts for relevant risk factors, which is then encoded before the system is used to evaluate real data. For example, a number of sample segmented patterns may be provided to a set of radiologists to evaluate the accuracy of the expert system's assignment. In this process, images such as two-dimensional slices of the three-dimensional shape of the segments are provided to the radiologists for identification. Based on the identifications performed by them, this information is used to train the evaluation system's pattern recognition algorithm. In separate embodiments of the invention, the feature recognition techniques described in detail in the subsection below devoted to the interpretation of the multidimensional field are also used to perform the identification of the initial shape estimate.

The final substep 34 in injecting physiological data is actually to assign nominal physiological values to each segment. These physiological values can be any relevant quantities that are to be generated in the final multidimensional field $q[r,t:\Theta(r,t)]$. In one embodiment where ultrasound is used to identify medical pathologies in tissue, these physiological quantities can be the sound speed and sound absorption. These quantities are more conveniently discussed in terms of a complex sound velocity v, in which $\Re(v)$ is the sound speed and $\Im(v)$ is related to the sound absorption constant, each of which may vary within the object under study. Thus, in this particular embodiment of the invention, the multidimensional field $q[r,t:\Theta(r,t)]$ of concern describes this complex sound velocity, $q[r,t:v(r,t)]$, at every voxel in the object under study.

The assignment of a nominal value of v can be accomplished by reference to a predetermined mapping between a morphologically assigned segment and a complex sound velocity. As will be understood by those skilled in the art, and as demonstrated in FIG. 7 for the case of acoustic waves, there is in reality variation in the complex sound velocity for different tissues, which is why the assignment at this step in the method is merely nominal. This figure is shown for illustration purposes in two dimensions (sound speed and absorption), although it will be readily apparent to those of skill in the art that the relationship may be generalized to arbitrarily many dimensions provided each of those additional dimensions bears on the identification of a particular tissue.

It will also be readily appreciated that similar relationships may be constructed for different types of medical pathologies and involving different physical parameters, and the invention encompasses the use of all such relationships in this context. In an even broader sense, this relationship can be expanded to include even the raw data, such as phase changes and amplitude changes, although there is, of course, a possibility that some of these quantities will then be highly correlated with each other. After the injection of the physiological data according to this method, a new estimate of the three-dimensional field, now termed a "physiological" estimate, $q_1^{est}[r,t:\Theta(r,t)]$ has been calculated.

The next step 16 of the method is the first step in the iterative portion of the method. At this step, the existing model of the object under study is used to calculate what detector data would be produced if the model multidimensional field corresponded exactly to the actual field of the object under study. In the particular embodiment where the waves are ultrasonic waves, this can be accomplished by using any appropriate sound-wave propagation codes. For those embodiments of the invention directed at the use of ultrasonic radiation, appropriate codes are available at various United States National Laboratories, including the Lawrence Livermore National Laboratory, Oak Ridge National Laboratory, Los Alamos National Laboratory, and Sandia National Laboratory. Other ultrasonic propagation codes are available at the Institut Francais Du Petrole in France, the National Oceanic and Atmospheric Administration, [See R. M. Jones, et al., HARPO: *A Versatile three-dimensional Hamiltonian ray-tracing program for acoustic waves in an ocean with irregular bottom*, NOAA Special Report PB87-172573/LL (1986), which is herein incorporated by reference], and from Computational Fluid Dynamics Research in Huntsville, Ala. A widely available code is the LINUX Ocean Acoustics and Seismic Exploration Synthesis Package. A full version of this code is available for licensing through the MIT Technology Licensing Office, Massachusetts Institute of Technology, Five Cambridge Center, Kendall Square, Room NE25-230, Cambridge Mass. 02142-1493. One feature in common with existing ultrasound propagation codes is that they contain a complex body of algorithms that can be used to input the estimated field $q_n^{est}[r,t:\Theta(r,t)]$, as well as both the configuration of sources and detectors and the characteristics of the ultrasound waves that were generated by the sources, so as to calculate the waveform of ultrasonic waves that will arrive at each detector. In alternative embodiments, more sophisticated features of such codes can be used to model the effects of noise and uncertainty on the propagated waves. The result of this step in the method is to produce an estimate of the detected signals $\{S_i^{(n)}\}$ that can be compared with the actual detected signals $\{S_i^{(0)}\}$.

The next step 18 in the method is to calculate the difference between the estimated signals and the actual signals: $\{\epsilon_i\}=\{S_i^{(0)}-S_i^{(n)}\}$. This error set is then tested in step 20 to determine whether the difference between the estimated signals and the actual signals is less than the noise. If so, then the iteration is deemed to have converged to its final value for construction of the rendering of the multidimensional field $q[r,t:\Theta(r,t)]$. If not, then the iteration proceeds for an additional step. To determine whether the error field is within the noise, the following quantity is compared against some predetermined threshold T:

$$\sum_i \frac{|S_i^{(n)} - S_i^{(0)}|^2}{V_{S_i^{(n)}} + V_{S_i^{(0)}}} < T$$

where $V_{Si}$ is the variance for the set $\{S_i\}$.

Figure 8:
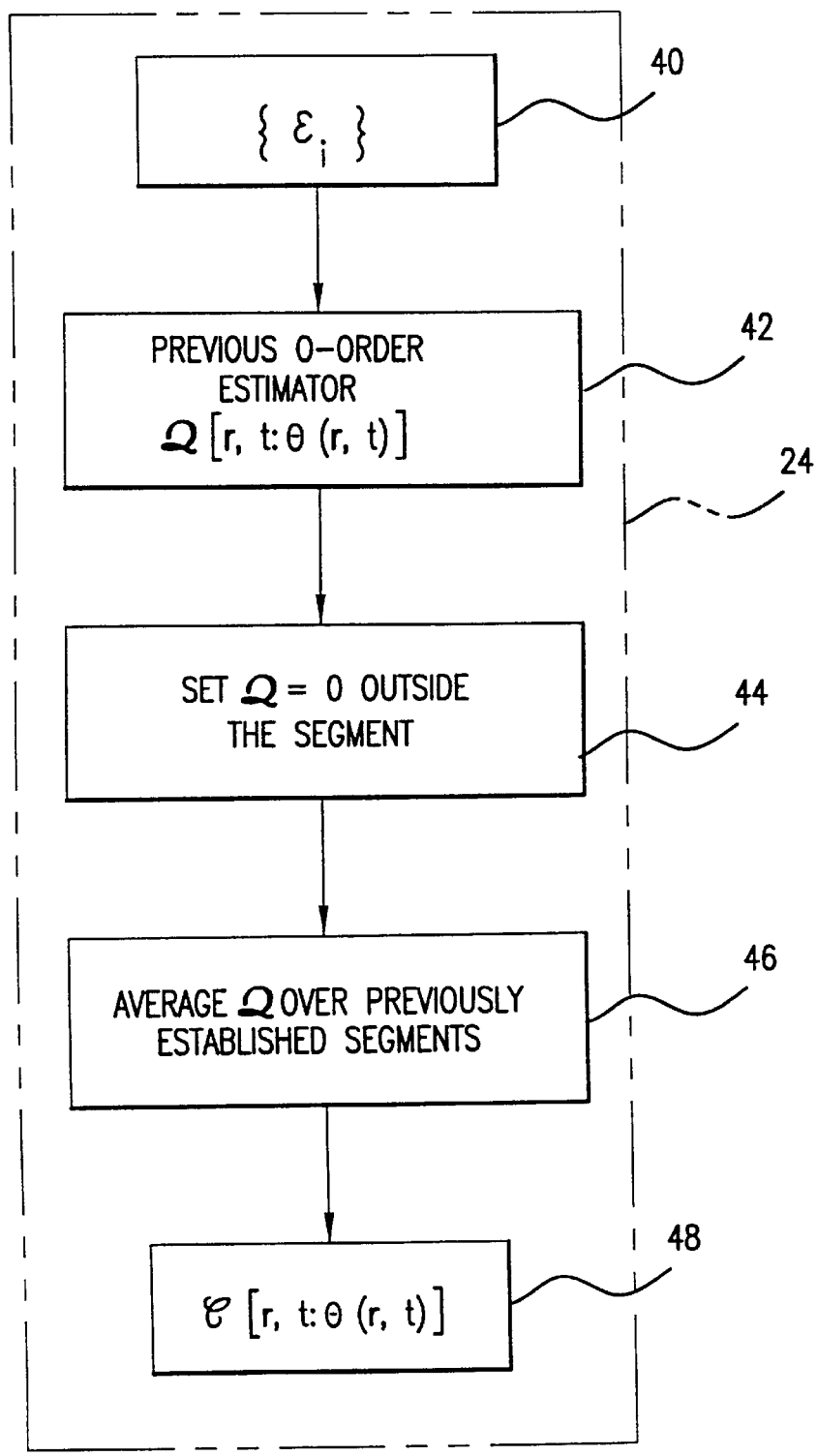
FIG. 8 is a flowchart illustrating in detail a method for changing the physiological data in the iterative part of the construction of the rendering of the multidimensional field $q[r,t:\Theta(r,t)]$.
Figure 9A:
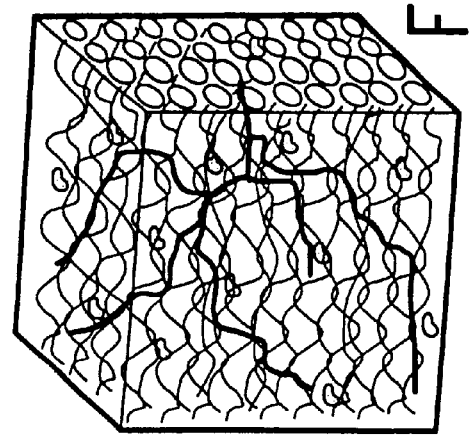
FIG. 9 shows a perspective view of morphing ultrasound fields. In part (a) and part (c), a representation of features in tissue are displayed at an initial time; in part (b) and part (d), the features are shown at a later time. No cancer growth is detected in part (b), but cancer is detected in part (d).
Figure 9C:
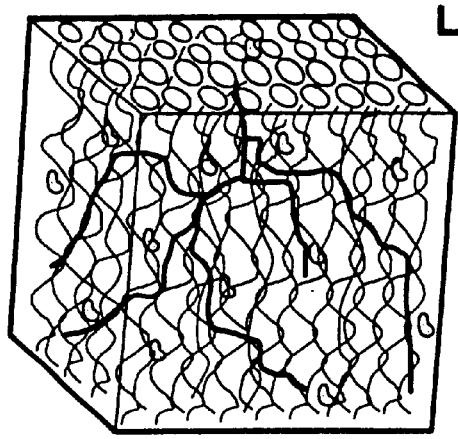
Figure 9B:
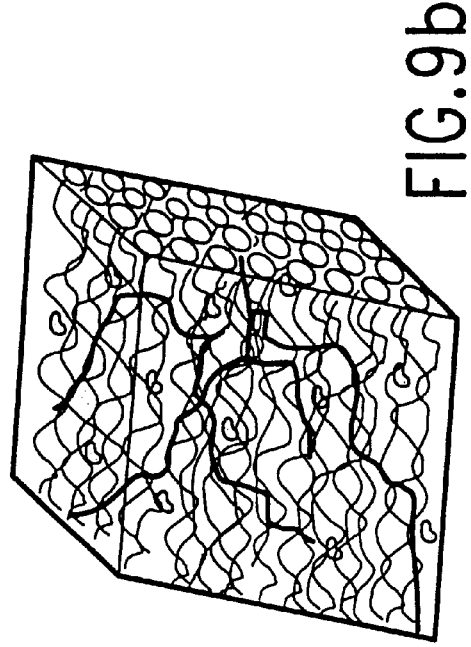
Figure 9D:
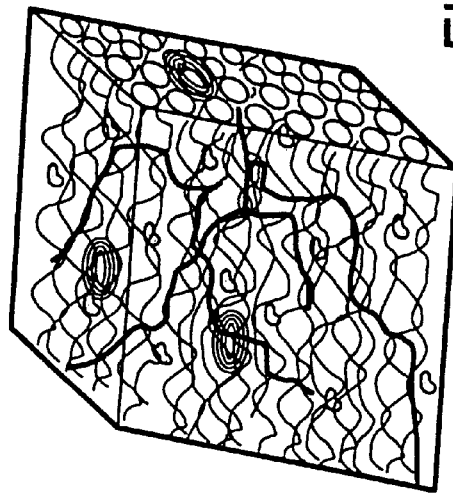

If the estimated field fails to produce a set of estimated detected signals that is consistent with the actual signals, at least within the noise level, then the physiological data are changed in order to improve the estimate in step 24. The method of changing the physiological data is shown in greater detail in FIG. 8. In this step, the method begins with the set of error signals at substep 40, which is used in an ultrasound propagation code at substep 42 to produce a correction field $\mathcal{Q}[r,t:\Theta(r,t)]$. Although in one embodiment, the same ultrasound propagation code will be used as was used at step 16, this is not a requirement of the invention, and a different ultrasound propagation code may be used in different embodiments. The previously assigned segmentation of the field is now used to refine the correction field at substep 44 so that $\mathcal{Q}[r,t:\Theta(r,t)]=0$ outside the segments. Inside the previously established segments, the correction field is averaged to produce the refinement field $<\mathcal{Q}[r,t:\Theta(r,t)]>\equiv\mathcal{C}[r,t:\Theta(r,t)]$.

In the final step 26 of the basic method, a new multidimensional field $q_{n+1}^{est}[r,t:\Theta(r,t)]$ is calculated by adding the refinement field to the previous multidimensional field:

$$q_{n+1}^{est}[r,t:\Theta(r,t)]=q_n^{est}[r,t:\Theta(r,t)]+\mathcal{C}[r,t:\Theta(r,t)].$$

The method then proceeds iteratively with this new multidimensional field used at step 16 to calculate the detected signals as if it were the actual field using some available ultrasound propagation code. The method iterates until the error field is such that it is deemed to be within the level of noise as defined by the threshold T. It will be readily appreciated by those of skill in the art that the ability of the method to converge and the speed of convergence will depend significantly on the quality of the initial estimate $q[r,t:\Theta_0(r,t)]$.

There are several different embodiments of this invention that will be understood by those of skill in the art. In one embodiment, there is cycling between different estimators at steps 16 or 42 in order to improve the estimate of the multidimensional field $q^{est}[r,t:\Theta(r,t)]$ and to combine the results of such estimators with techniques such as Bayesian or Kalman filtering, covariance intersection, or some form of fuzzy combination. See, for example, James V. Candy, *Signal Processing: The Model-Based Approach* (McGraw Hill, 1986), which is herein incorporated by reference.

There are also alternative methods that can also be used to construct the multidimensional field. All such methods can be broadly categorized as falling into one of two classes. In the first class, into which the method described in detail above falls, the method begins with an initial approximation that is progressively improved. In the second class of methods, the system is permitted to vary essentially randomly and individual multidimensional field constructions that develop during the process are evaluated to determine which best reproduces the observed data. An example of such a method is a genetic algorithm.

The genetic algorithm is a model of machine learning that derives its behavior in an attempt to mimic evolution in nature. See, for example, Melanie Mitchell, *An Introduction to Genetic Algorithms* (Complex Adaptive Systems, 1996), which is herein incorporated by reference. This is done by generating a population of individuals represented by chromosomes, in essence a set of character strings that are analogous to the base-four chromosomes of DNA. The individuals in the population then go through a process of simulated "evolution." The genetic algorithm is widely used in multidimensional optimization problems in which the character string of the chromosome can be used to encode the values for the different parameters being optimized. In practice, therefore, an array of bits or characters to represent the chromosomes, in this case the multidimensional field $q[r,t:\Theta(r,t)]$, is provided; then bit manipulation operations allow the implementation of crossover, mutation, and other operations.

When the genetic algorithm is implemented, it is trained in a manner that involves the following cycle: the fitness of all individuals in the population is first evaluated; then, a new population is created by performing operations such as crossover, fitness-proportionate reproduction, and mutation on the individuals whose fitness has just been measured; finally, the old population is discarded and iteration is performed with the new population. One iteration of this loop is referred to as a generation. In the present invention, a number of randomly generated multidimensional fields $q[r,t:\Theta(r,t)]$ are used as the initial input. This population of fields is then permitted to evolve as described above, with each individual field being tested at each generation to see if it can adequately reproduce the observed data. This is done in precisely the same manner as described above, with a wave-propagation code being used to generate a set of data $\{S_i^{(n)}\}$ that is compared with the actual observed data $\{S_i^{(o)}\}$. The genetic algorithm may be used as an alternative embodiment of the invention to generate the multidimensional field $q[r,t:\Theta(r,t)]$.

It will readily be understood by those of skill in the art that the most appropriate technique to use in constructing the multidimensional field rendering will depend greatly on the speed of the technique in light of the computational capacity of the hardware and software that is used to perform the computations. While the invention has been described in detail with specific examples of how to construct the multidimensional field, the invention is not so limited and encompasses alternative schemes to do so.

3. Interpretation of the Multidimensional Field $q[r,t:\Theta(r,t)]$

Figure 7:
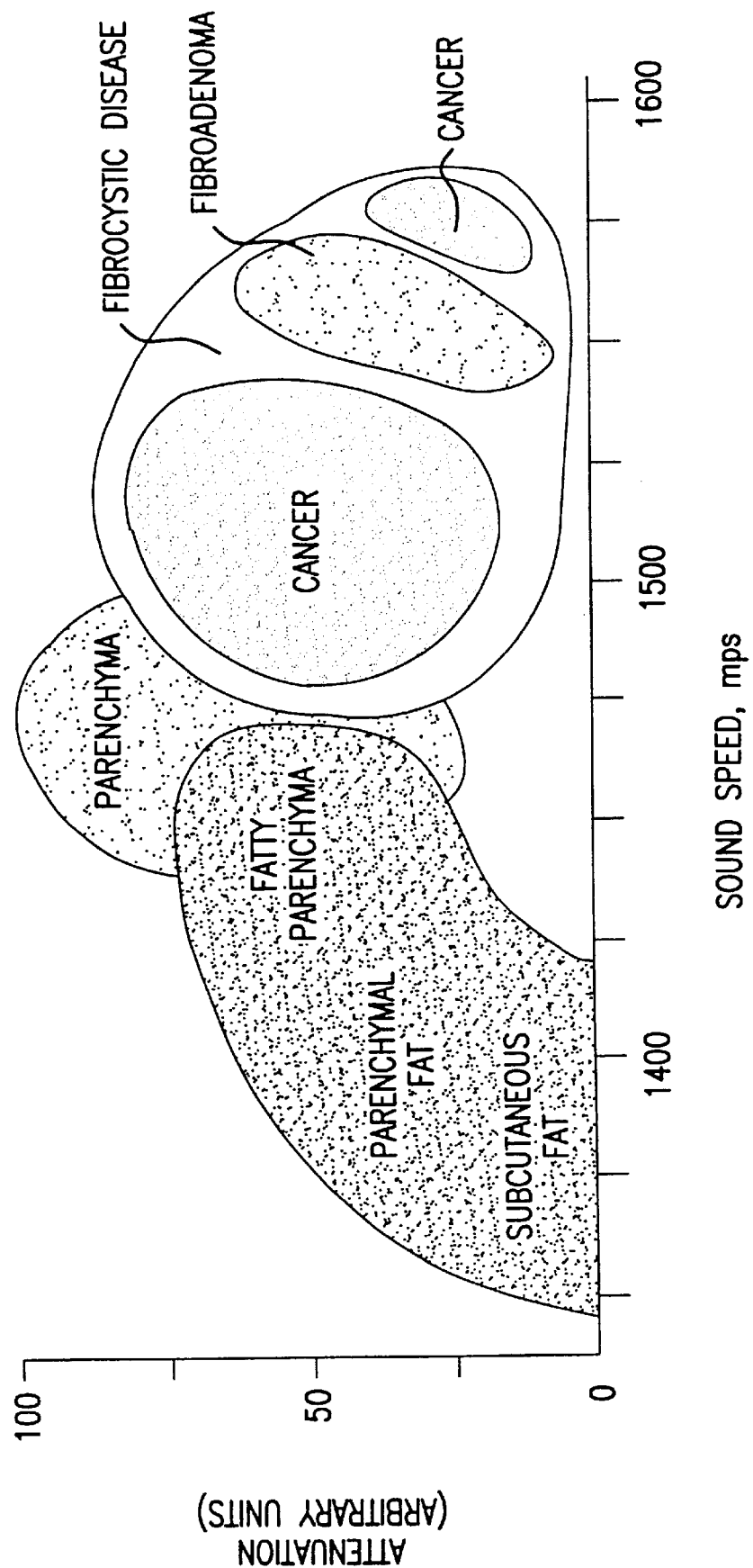
FIG. 7 is a graph showing the relationship between the ultrasonic complex sound velocity (sound speed and absorption) and the type of tissue that is found in the human breast.

As a result of determining the multidimensional field $q[r,t:\Theta(r,t)]$, an interpretation is made of the physical characteristics $\Theta$ that make up the field $q[r,t:\Theta(r,t)]$. The interpretations that can be drawn are related directly to the types of physical quantities that have been calculated in $q[r,t:\Theta(r,t)]$ and the existence of a trained evaluation system that can take that information to develop interpretations. Without intending to limit the scope of the invention, this can best be illustrated by describing the embodiment where the multidimensional field describes the complex sound velocity for ultrasound waves that have been scattered off of the tissues within a human breast, $v(r,t)$. The relationship between the complex sound velocity and the interpretation of what features exist in the breast is shown by FIG. 7. Given the complex sound velocity, this relationship is used to classify tissue types. There is no a priori reason to expect that this relationship will be of a simple functional form that can be reduced to an equation, and therefore a mapping from the complex sound velocity onto this interpretation requires the use of more sophisticated techniques. These can include the use of neural nets; stochastic optimization, wherein the shape of curves encompassing certain interpretations is changed by using methods such as steepest descent or simulated annealing; or evolutionary methods, wherein that shape is changed by the genetic algorithm described above for evolving the multidimensional field. See generally, Stanley R. Deans, *The Radon Transform and Some of Its Applications* (Krieger Publishing, 1993), which is herein incorporated by reference.

One method of interpreting the multidimensional field involves probabilistic estimation. The basic concept of probabilistic estimators is to designate the regions of the voxels in terms of probabilities of certain tissue classifications given a certain input value of $q[r,t:\Theta(r,t)]$. For instance, given a set of values for a particular voxel, the probability that that voxel represents a particular interpretation is first determined. The voxel is then identified as the region with the highest probability. Test information is used to generate the basic probabilities. For example, in the embodiment where ultrasound is used to study breast tissue, there is a probability of certain types of tissue or tissue pathologies based on the calculated complex sound velocities for the individual voxels.

In more specialized stochastic estimation schemes, some regions are given more weight than others in order to reduce the rate of false positives or negatives. It will readily be understood that in different embodiments of the invention, it is more desirable to minimize either the rate of false positives or the rate of false negatives. For example, in the particular embodiment where cancer is to be identified in tissue, some level of false positives may be acceptable since a positive identification of cancer will be followed by additional medical procedures; however, it is desirable that the level of false negatives be minimized.

In an alternative embodiment, a neural net is used to interpret the multidimensional field. See, for example, Simon S. Hagkin, *Neural Networks—A Comprehensive Foundation* (Prentice Hall, 1998), which is herein incorporated by reference. In that case, it is necessary to train the neural net to be able to perform the identification accurately and consistently. A typical neural network includes a plurality of nodes, and each node has a weight value associated with it. One layer is an input layer having a plurality of input nodes, and another layer is an output layer having a plurality of output nodes, with at least one layer therebetween. In this example, the input nodes receive the multidimensional field values $q[r,t:\Theta(r,t)]$ (the complex sound velocity in the exemplary embodiment) and the output node generates an interpretation designation (tissue type in the exemplary embodiment). In other words, given an input comprising the multidimensional field values of one voxel, the input is combined (added, multiplied, subtracted in a variety of combinations and iterations depending upon how the neural network is initially organized), and then the interpretation is generated accordingly.

In order to train the neural net, the output values are compared against the correct interpretation with some known samples. If the output value is incorrect when compared against such a test interpretation, the neural net modifies itself to arrive at the correct output value. This is achieved by connecting or disconnecting certain nodes and/or adjusting the weight values of the nodes during the training through a plurality of iterations. Once the training is completed, the resulting layer/node configuration and corresponding weights represents a trained neural net. The trained neural net is then ready to receive unknown multidimensional-field data and designate interpretations for each voxel. Classical neural nets include Kohonen nets, feed-forward nets, and back-propagation nets. The different neural nets have different methods of adjusting the weights and organizing the respective neural net during the training process.

In the embodiment of the invention where ultrasound is used to study breast tissue, a second method based on Hough transformation is used to increase the probability that a cancerous tumor has been found. See, for example, Stanley R. Deans, *The Radon Transform and Some of Its Applications* (Krieger Publishing, 1993), which is herein incorporated by reference. The basic concept in this embodiment is that closed volumes are identified in the tissue since such closed volumes are indicative of the existence of neoplasms. This information is then coupled with a complex sound velocity that is suggestive of cancer in order to increase the reliability of the interpretation that the identified neoplasm is a malignancy.

A closed volume may be represented as an ellipsoid where r=(x, y, z):

$$\left(\frac{x-x_o}{A}\right)^2 + \left(\frac{y-y_o}{B}\right)^2 + \left(\frac{z-z_o}{C}\right)^2 = 1$$

It will be apparent to those of skill in the art that for a fixed $(x_0, y_0, z_0, A, B, C)$, each $(x, y, z)$ that satisfies the equation defines a point on the surface of an ellipsoid. However, it is also true that every point on the surface of an object will define a curve in the six-dimensional space where $(x_0, y_0, z_0, A, B, C)$ are the variables. If the object is a true ellipsoid, then all of these curves will intersect at a single point. Deviations from a true ellipsoid manifest themselves as curves that do not pass through the point. In order to identify a closed volume, therefore, it is simply necessary to examine the clumping of curves defined by mapping each point into this six-dimensional space. Whenever clumping of the curves is detected, there is a likelihood that a closed volume exists in real three-dimensional space.

Once a closed volume has been recognized, it is useful also to calculate the quasifractal dimension of the surface of the volume. This calculation may increase the probability that cancer has been identified because the surface properties of tumors differ, with benign tumors generally being smooth, unlike malignant tumors. Thus, if the quasifractal dimension is near 2, then the surface is smooth and the volume is unlikely to be cancerous. If the quasifractal dimension is greater than 2, then the surface is fuzzy, and there is a greater probability that the closed volume that has been identified is cancerous.

Another useful characteristic to extract from the multidimensional field, and a third method that can be used for the identification of cancer, is the existence of angiogenesis. This is useful because an identification of regional increased blood flow serves as an indication that this is due to tumor recruitment. See Louvar et al, *Correlation of color Doppler flow in the prostate with tissue microvascularity, Cancer* 1998 July 1:83(1): 135–40, which is herein incorporated by reference. The relevant information needed to make this identification is extracted from the multidimensional field when the radiation detectors have been designed to detect frequency since this then allows the use of the Doppler effect, as described above, to recognize the motion of fluids, particularly blood, in the organ.

Specifically, the multidimensional field in this instance will include a component that contains the frequency shift or velocity of the features throughout the organ. The trained evaluation system can then identify those regions where the fluid velocity is pronounced and patterned in a geometrical configuration that matches other tumor indicators such as the closed volume discussed above, thereby identifying angiogenesis. The ability of such a system to identify angiogenesis is enhanced greatly by the three-dimensional nature of the field construction of the invention as well as the large solid angle coverage of the invention. In other, two-dimensional imaging systems, the Doppler information is limited because it is unable to use information derived from any component of motion that is orthogonal to the plane of the two-dimensional image.

Confidence in the identification of angiogenesis may be increased by correlating the Doppler information from the multidimensional field with information in the multidimensional field related to tissue pressure as a fourth method of cancer identification. Tissue pressure is another relevant component in the identification of malignant tumors, and can be determined from an examination of subharmonic signal amplitude. The existence of a correlation between the subharmonic signal amplitude in ultrasonic studies with tissue pressure has been demonstrated in W. T. Shi et al., *Effects of Pressure Changes on Harmonic and Subharmonic Response of US Contrast Microbubbles, Radiology Supplement*, 1154 (1999), which is herein incorporated by reference.

The Doppler sensitivity of the system to motion is also important in the identification of cancer for another reason, which serves as a fifth method of cancer identification. When vibrations are applied to the tissues at a known frequency as described above, the invention permits recognition of the tougher tissues that are associated with the early tendency of cancer to attach to its surrounding normal tissues. In particular, the Doppler effect is useful in this context because microcalcifications in tissue produce well-defined high contrast with the surrounding tissue when external vibrations are applied. This is described in C. M. Sehgal et al., *Visualization of Breast Calcification by Acoustic Resonance Imaging, Radiology Supplement*, 1150 (1999), which is herein incorporated by reference. Near vibration resonance frequencies of 70–250 Hz, the Doppler signal for such microcalcifications is 5–6 times greater than for surrounding tissue, permitting good discrimination of such features.

In a sixth method of cancer identification, the electrical impedance in tissue is extracted from the multidimensional field. The electrical impedance of tissue may be used as a factor to identify tumors, as described in Jeremy C. Hebden et al., *Acoustically modulated electrical impedance tomography, Proceedings of the SPIE*, 1231:7–14 (1990), which is herein incorporated by reference.

In a seventh method of cancer identification, the resolution can be improved by comparing the measurements of the object under examination made at two different times. The rendering of the multidimensional field $q[r,t:\Theta(r,t)]$ is constructed for each set of measurements, and the fields are compared. This will require storing of at least the original raw data, registration of the original raw data to the new raw data, and comparing the original and new raw data for the purpose of ascertaining changes between the two different times. Although it is possible in principle to store the original raw data directly, this would require a large data storage capacity. Alternatively, the original raw data can be stored by performing compression on the data.

Both lossy and lossless compression methods are available. For accuracy, lossless compression, such as by using the Joint Photographic Expert Group (JPEG) standard can be used, and for efficiency, lossy compression can be used. In particular, a fractal compression method can be used when a very high compression ratio is desired. The fractal compression method may represent the optimal compression method because it provides more accuracy in compressing images containing natural scenes (e.g., the human breast). Conventional fractal compression methods may be readily adapted to the multidimensional field, which is dependent on three dimensions. In this method, each component of the field is compressed by dividing it into a plurality of uniformly sized blocks. Another method is to divide the components of the field using a quad-tree partition. The field is split into large blocks, and these blocks are split into smaller blocks if a suitably accurate match cannot be found. Matches are then attempted for these subblocks, and if none can be found, these subblocks are in turn divided into subblocks. The process continues until a minimum block size is reached, when a match may be made.

Each tissue volume contains ducts, blood vessels, calcifications, and other artifacts hat change very little, even over extended periods of time. However, the original data may not exactly match the new data due to changing of the overall shape, change in physical condition of the subject, etc. One method to ameliorate this problem is morphing of the original data to the conditions present when the new data were collected. Here, image morphing is the conventional image morphing method that blends a source image to a destination image by warping one or both images through a plurality of intermediate images. This is illustrated in FIG. 9, which is a perspective view of features in tissue. In parts (a) and (c) of the figure, the features have been constructed for observations at an initial time, and in parts (b) and (d) of the figure, the features have been constructed for observations made at a later time. In each case, there has been some change in the overall shape of the tissue sample. Differences manifest themselves, however, when the fields are morphed onto each other by using those artifacts that change little over time as landmarks. In part (b) of the figure, there is no significant change after the morphing, leading to the conclusion that there is no cancer growth. In part (d), however, there are significant changes that are apparent after morphing, leading to the conclusion that there has been anomalous change in the tissue sample.

After the multidimensional field is reconstructed for the original data, it can be compared with the multidimensional field generated for the new data. The difference between the two could be achieved by a simple subtraction of one from the other. Alternatively, the phase of the returned ultrasound signals could be used to perform interferometry to locate any changes. Also, if the two fields are generated from data taken relatively close in time (perhaps separated by only a few milliseconds), then the interferometry technique may be used to improve the resolution of the invention.

Each of these cancer-identification techniques can be evaluated independently by the trained evaluation system, such as an expert system computer program or self-learning neural network. The various factors may be combined with a variety of means of sensor fusion. As an illustration, when the trained evaluation system assigns a probability that cancer has been identified based on a number of independent factors, the reliability of the assignment can be increased by calculating a product of probabilities. For example if $p_k$ is the probability that a given feature is cancer based on identification technique k, then the probability P that the feature is cancer based on the use of multiple techniques is $$P = 1 - \Pi(1-p_k)$$

Further variations on the method exist. This includes modifying the emitted radiation in the sources so as to focus on areas that have been identified as suspicious, and thereby analyze them more closely. The method may be integrated with other techniques that are known, such as mammography. In this instance, the reliability of the identification is again improved by calculating a product of probabilities.

Although the invention has been particularly shown and described with reference to embodiments of the invention directed at the detection and characterization of medical pathologies, it will be understood by those of skill in the art that the method and apparatus described may also readily be applied to non-medical applications. In particular, the method and apparatus may be used to detect and characterize distinctive features within an object. This may be exemplified, without limitation of the invention, by an apparatus and method used for the detection and characterization of defects in aerospace devices. By providing a matched-impedance contact between the aerospace device and arrays of sources and detectors, the invention is used to irradiate or insonify the aerospace device. Data collected after the radiation has been scattered (which includes reflection, diffraction, and transmission of the radiation) is then be used to construct a multidimensional-field rendering of the aerospace device. This multidimensional-field rendering is then used to detect and characterize features, such as defects, within the aerospace device. Each of these steps is carried out in the manner particularly and distinctly described above with respect to medical applications.

While the invention has been particularly shown and described with reference to preferred embodiments thereof, it is well understood by those skilled in the art that various changes and modifications may be made in the invention without departing from the spirit and scope of the invention.

What is claimed is:

1. Method for destruction of a medical pathology within an object under study, comprising the steps of:
   (a) retrieving a multidimensional field rendering of a volume of the object under study constructed from data provided by a plurality of detectors disposed to surround at least a portion of such object;
   (b) characterizing such medical pathology based on said multidimensional field rendering; and
   (c) irradiating such medical pathology with high-intensity focused radiation to destroy such medical pathology.

2. The method recited in claim 1 wherein characterizing such medical pathology is accomplished by using an expert system.

3. The method recited in claim 1 wherein characterizing such medical pathology is accomplished by using a neural net.

4. The method recited in claim 1 wherein such data comprise ultrasound data.

5. The method recited in claim 1 wherein said object under study comprises a plurality of biological tissues.

6. The method recited in claim 5 wherein said multidimensional field rendering comprises sound speeds and sound absorptions for a plurality of volume elements occupied by said plurality of biological tissues.

7. The method recited in claim 5 wherein characterizing such medical pathology comprises classifying said plurality of biological tissues based on said multidimensional field rendering.

8. The method recited in claim 5 wherein characterizing such medical pathology comprises identifying closed volumes in said plurality of biological tissues based on said multidimensional field rendering.

9. The method recited in claim 8 wherein characterizing such medical pathology further comprises determining a quasifractal dimension of said closed volumes based on said multidimensional field rendering.

10. The method recited in claim 1 wherein such radiation comprises ultrasound radiation.

11. Method for destruction of a distinct feature within an object under study, comprising the steps of:
    (a) retrieving a multidimensional field rendering of a volume of the object under study constructed from data provided by a plurality of detectors disposed to surround at least a portion of such object;
    (b) characterizing such distinct feature based on said multidimensional field rendering; and
    (c) irradiating such distinct feature with high-intensity focused radiation to destroy such distinct feature.

12. The method recited in claim 11 wherein characterizing such distinct feature is accomplished by using an expert system.

13. The method recited in claim 11 wherein characterizing such distinct feature is accomplished by using a neural net.

14. The method recited in claim 11 wherein such data comprise ultrasound data.

15. The method recited in claim 11 wherein said multidimensional field rendering comprises sound speeds and sound absorptions for a plurality of volume elements occupied by said distinct features.

16. The method recited in claim 15 wherein characterizing such distinct feature comprises classifying said distinct feature based on said multidimensional field rendering.

17. The method recited in claim 15 wherein characterizing such distinct feature comprises identifying closed volumes in said object under study based on said multidimensional field rendering.

18. The method recited in claim 17 wherein characterizing such distinct feature further comprises determining a quasifractal dimension of said closed volumes based on said multidimensional field rendering.

19. The method recited in claim 11 wherein such radiation comprises ultrasound radiation.

* * * * *